(12) United States Patent
Sekine et al.

(10) Patent No.: US 8,724,870 B2
(45) Date of Patent: May 13, 2014

(54) OPHTHALMIC OBSERVATION APPARATUS

(75) Inventors: Akihiko Sekine, Tokyo (JP); Nobusuke Obata, Tokyo (JP); Katsuhiro Yamada, Tokyo (JP)

(73) Assignee: Kabushiki Kaisha-Topcon, Tokyo (JP)

( * ) Notice: Subject to any disclaimer, the term of this patent is extended or adjusted under 35 U.S.C. 154(b) by 112 days.

(21) Appl. No.: 13/387,007

(22) PCT Filed: Jul. 14, 2010

(86) PCT No.: PCT/JP2010/004579
§ 371 (c)(1),
(2), (4) Date: Jan. 25, 2012

(87) PCT Pub. No.: WO2011/013314
PCT Pub. Date: Feb. 3, 2011

(65) Prior Publication Data
US 2012/0121158 A1 May 17, 2012

(30) Foreign Application Priority Data
Jul. 29, 2009 (JP) .................................. 2009-176201

(51) Int. Cl.
*G06K 9/00* (2006.01)
*A61B 3/14* (2006.01)
*A61B 3/10* (2006.01)

(52) U.S. Cl.
USPC ............................ 382/128; 351/206; 351/211

(58) Field of Classification Search
CPC ....................................................... A61B 3/185
USPC ................................... 382/131; 351/205, 206
See application file for complete search history.

(56) References Cited

U.S. PATENT DOCUMENTS

| | | |
|---|---|---|
| 6,377,349 B1 | 4/2002 | Fercher |
| 7,345,770 B2 | 3/2008 | Chan et al. |
| 2004/0004694 A1 | 1/2004 | Sugino et al. |

(Continued)

FOREIGN PATENT DOCUMENTS

| | | |
|---|---|---|
| JP | 06-237900 A | 8/1994 |
| JP | 09-276232 A | 10/1997 |

(Continued)

OTHER PUBLICATIONS

International Search Report for PCT/JP2010/004579; mailed Oct. 12, 2010.

(Continued)

Primary Examiner — Vu Le
Assistant Examiner — Soo Park
(74) Attorney, Agent, or Firm — Pearne & Gordon LLP

(57) ABSTRACT

An ophthalmic observation apparatus 1 performs an OCT measurement of a fundus Ef to form an OCT image, performs an analytical processing on this OCT image, and outputs examination-results information including the analysis results. The ophthalmic observation apparatus 1 is capable of selectively executing a plurality of operation modes. The ophthalmic observation apparatus 1 preliminarily stores operation mode information 214, in which various operational details are associated with each operation mode. When one operation mode is designated, the ophthalmic observation apparatus 1 refers to the operation mode information 214 to identify the operational details associated with this operation mode, and controls an optical system, an image forming part 220, a three-dimensional image forming part 231, an analytic processor 232, a display 240, and/or a printer 300, etc. based on the identified operational details.

17 Claims, 6 Drawing Sheets

| OPERATION ITEM<br>MODE | FIXATION<br>DIRECTION | SCANNING<br>PATTERN | IMAGE TYPE | ANALYTIC<br>PROCESS | INFORMATION TYPE | DISPLAY<br>LAYOUT | PRINT<br>LAYOUT |
|---|---|---|---|---|---|---|---|
| MACULAR EXAMINATION MODE | MACULA FIXATION DIRECTION | •3D<br>•RADIAL<br>•LINE | •FUNDUS IMAGE<br>•TOMOGRAPHIC IMAGE<br>•3D IMAGE | •RETINAL THICKNESS ANALYSIS<br>•NORMATIVE DATA COMPARISON | •FUNDUS IMAGE<br>•REPRESENTATIVE TOMOGRAPHIC IMAGE<br>•NORMATIVE COMPARISON DIAGRAM | MACULAR EXAMINATION TEMPLATE | MACULAR EXAMINATION TEMPLATE |
| OPTIC-DISC EXAMINATION MODE | OPTIC-DISC FIXATION DIRECTION | •CIRCLE<br>•3D | •FUNDUS IMAGE<br>•TOMOGRAPHIC IMAGE<br>•3D IMAGE | •RNFL THICKNESS ANALYSIS<br>•NORMATIVE DATA COMPARISON<br>•OPTIC-DISC SHAPE ANALYSIS | •FUNDUS IMAGE<br>•REPRESENTATIVE TOMOGRAPHIC IMAGE<br>•NORMATIVE COMPARISON DIAGRAM<br>•OPTIC-DISC SHAPE PARAMETERS | OPTIC-DISC EXAMINATION TEMPLATE | OPTIC-DISC EXAMINATION TEMPLATE |
| GLAUCOMA EXAMINATION MODE | •MACULA FIXATION DIRECTION<br>•OPTIC-DISC FIXATION DIRECTION | •MACULA 3D<br>•OPTIC DISC 3D | •FUNDUS IMAGE<br>•TOMOGRAPHIC IMAGE<br>•3D IMAGE | •RNFL THICKNESS ANALYSIS<br>•NORMATIVE DATA COMPARISON<br>•OPTIC-DISC SHAPE ANALYSIS | •FUNDUS IMAGE (MOSAIC IMAGE)<br>•REPRESENTATIVE TOMOGRAPHIC IMAGE<br>•NORMATIVE COMPARISON DIAGRAM (FUNDUS IMAGE SUPERIMPOSITION)<br>•OPTIC-DISC SHAPE PARAMETERS | GLAUCOMA DIAGNOSIS TEMPLATE | GLAUCOMA DIAGNOSIS TEMPLATE |
| MACULAR-DEGENERATION EXAMINATION MODE | MACULA FIXATION DIRECTION | •3D | •FUNDUS IMAGE<br>•TOMOGRAPHIC IMAGE<br>•3D IMAGE | •RETINAL THICKNESS ANALYSIS<br>•DRUSEN ANALYSIS | •FUNDUS IMAGE (DRUSEN DISPLAY)<br>•REPRESENTATIVE TOMOGRAPHIC IMAGE<br>•DRUSEN DISTRIBUTION GRAPH/TABLE | MACULAR DEGENERATION DIAGNOSIS TEMPLATE | MACULAR DEGENERATION DIAGNOSIS TEMPLATE |

214

(56) References Cited

U.S. PATENT DOCUMENTS

| | | |
|---|---|---|
| 2008/0030680 A1* | 2/2008 | Tsukada et al. ............... 351/206 |
| 2008/0084538 A1 | 4/2008 | Maeda et al. |
| 2008/0151187 A1 | 6/2008 | Tsukada et al. |
| 2008/0204655 A1 | 8/2008 | Kikawa et al. |
| 2008/0259275 A1 | 10/2008 | Aoki et al. |
| 2008/0312552 A1 | 12/2008 | Zhou et al. |
| 2009/0033868 A1* | 2/2009 | Huang et al. .................. 351/205 |
| 2009/0190092 A1 | 7/2009 | Tsukada et al. |
| 2010/0039616 A1* | 2/2010 | Yumikake et al. ............ 351/206 |
| 2010/0118132 A1 | 5/2010 | Yumikake et al. |

FOREIGN PATENT DOCUMENTS

| | | |
|---|---|---|
| JP | 11-325849 A | 11/1999 |
| JP | 2002-139421 A | 5/2002 |
| JP | 2004-147829 A | 5/2004 |
| JP | 2006-153838 A | 6/2006 |
| JP | 2007-024677 A | 2/2007 |
| JP | 2007-252692 A | 10/2007 |
| JP | 2007-325831 A | 12/2007 |
| JP | 2008-073099 A | 4/2008 |
| JP | 2008-86670 A | 4/2008 |
| JP | 2008-167777 A | 7/2008 |
| JP | 2008-206684 A | 9/2008 |
| JP | 2008-237237 A | 10/2008 |
| JP | 2008-259544 A | 10/2008 |
| JP | 2008-267892 A | 11/2008 |
| JP | 2008-289642 A | 12/2008 |
| JP | 2008-295804 A | 12/2008 |
| JP | 2009-061203 A | 3/2009 |
| JP | 2009-066015 A | 4/2009 |
| WO | WO 2008129863 A1 * | 10/2008 |

OTHER PUBLICATIONS

Extended European Search Report for 10804067.6—1554/2460460 dated Feb. 22, 2013.
Japanese Office Action for Application No. JP 2009-176201 dated Feb. 12, 2013.

* cited by examiner

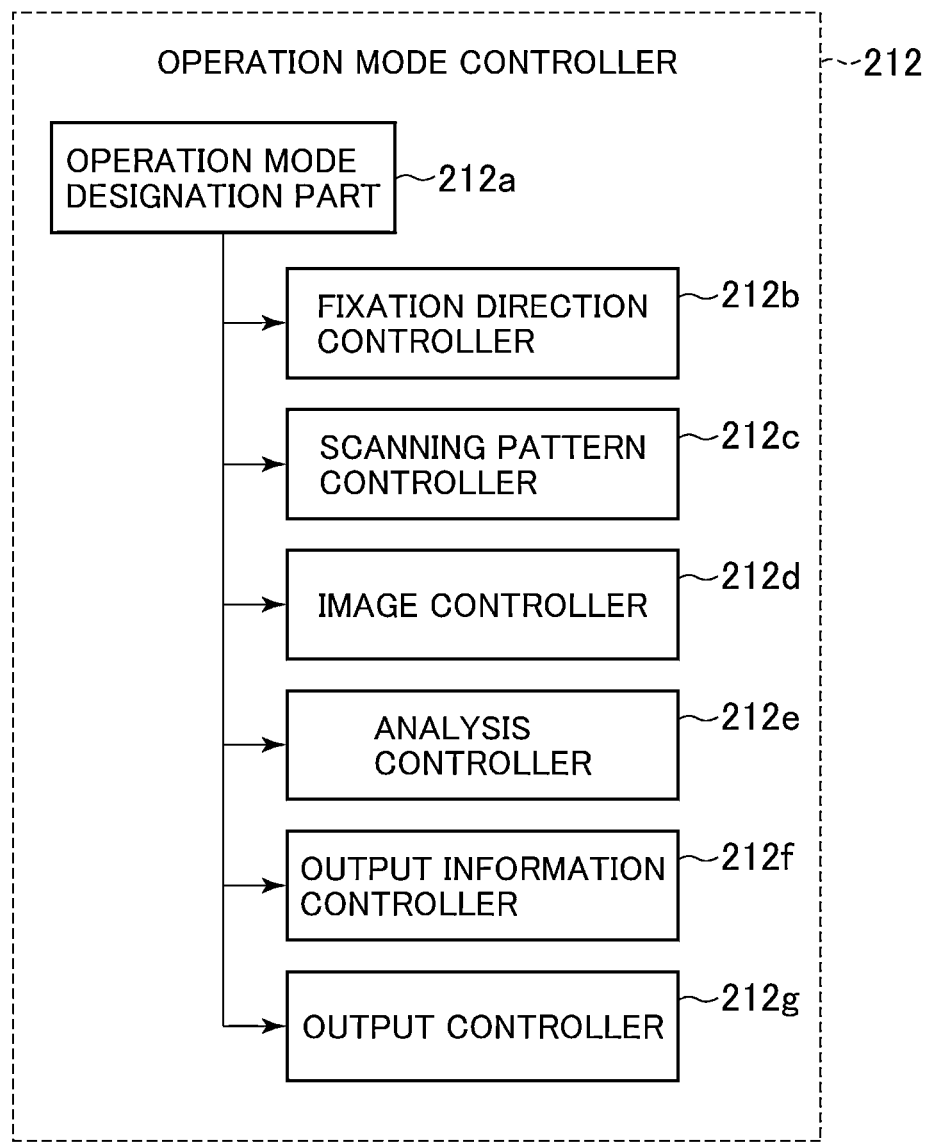

| OPERATION ITEM / MODE | FIXATION DIRECTION | SCANNING PATTERN | IMAGE TYPE | ANALYTIC PROCESS | INFORMATION TYPE | DISPLAY LAYOUT | PRINT LAYOUT |
|---|---|---|---|---|---|---|---|
| MACULAR EXAMINATION MODE | MACULA FIXATION DIRECTION | • 3D<br>• RADIAL<br>• LINE | • FUNDUS IMAGE<br>• TOMOGRAPHIC IMAGE<br>• 3D IMAGE | • RETINAL THICKNESS ANALYSIS<br>• NORMATIVE DATA COMPARISON | • FUNDUS IMAGE<br>• REPRESENTATIVE TOMOGRAPHIC IMAGE<br>• NORMATIVE COMPARISON DIAGRAM | MACULAR EXAMINATION TEMPLATE | MACULAR EXAMINATION TEMPLATE |
| OPTIC-DISC EXAMINATION MODE | OPTIC-DISC FIXATION DIRECTION | • CIRCLE<br>• 3D | • FUNDUS IMAGE<br>• TOMOGRAPHIC IMAGE<br>• 3D IMAGE | • RNFL THICKNESS ANALYSIS<br>• NORMATIVE DATA COMPARISON<br>• OPTIC-DISC SHAPE ANALYSIS | • FUNDUS IMAGE<br>• REPRESENTATIVE TOMOGRAPHIC IMAGE<br>• NORMATIVE COMPARISON DIAGRAM<br>• OPTIC-DISC SHAPE PARAMETERS | OPTIC-DISC EXAMINATION TEMPLATE | OPTIC-DISC EXAMINATION TEMPLATE |
| GLAUCOMA EXAMINATION MODE | • MACULA FIXATION DIRECTION<br>• OPTIC-DISC FIXATION DIRECTION | • MACULA 3D<br>• OPTIC DISC 3D | • FUNDUS IMAGE<br>• TOMOGRAPHIC IMAGE<br>• 3D IMAGE | • RNFL THICKNESS ANALYSIS<br>• NORMATIVE DATA COMPARISON<br>• OPTIC-DISC SHAPE ANALYSIS | • FUNDUS IMAGE (MOSAIC IMAGE)<br>• REPRESENTATIVE TOMOGRAPHIC IMAGE<br>• NORMATIVE COMPARISON DIAGRAM (FUNDUS IMAGE SUPERIMPOSITION)<br>• OPTIC-DISC SHAPE PARAMETERS | GLAUCOMA DIAGNOSIS TEMPLATE | GLAUCOMA DIAGNOSIS TEMPLATE |
| MACULAR-DEGENERATION EXAMINATION MODE | MACULA FIXATION DIRECTION | • 3D | • FUNDUS IMAGE<br>• TOMOGRAPHIC IMAGE<br>• 3D IMAGE | • RETINAL THICKNESS ANALYSIS<br>• DRUSEN ANALYSIS | • FUNDUS IMAGE (DRUSEN DISPLAY)<br>• REPRESENTATIVE TOMOGRAPHIC IMAGE<br>• DRUSEN DISTRIBUTION GRAPH/TABLE | MACULAR DEGENERATION DIAGNOSIS TEMPLATE | MACULAR DEGENERATION DIAGNOSIS TEMPLATE |

OPHTHALMIC OBSERVATION APPARATUS

TECHNICAL FIELD

The present invention relates to an ophthalmic observation apparatus configured to form images of a subject eye by using optical coherence tomography (OCT).

BACKGROUND ART

In recent years, OCT that forms images of the surface morphology and internal morphology of an object by using a light beam from a laser light source or the like has attracted attention. Unlike an X-ray CT apparatus, OCT is noninvasive to human bodies, and is therefore expected to be utilized in the medical field and biological field. For example, in the ophthalmology, apparatuses that form images of a fundus and a cornea are in a practical stage.

Patent Document 1 discloses a device to which OCT is applied. This device has such a configuration that: a measuring arm scans an object by a rotary deflection mirror (a Galvano mirror); a reference arm is provided with a reference mirror; and an interferometer is mounted at the outlet to analyze, by a spectrometer, the intensity of an interference light of light fluxes from the measurement arm and the reference arm. Moreover, the reference arm is configured to gradually change the light flux phase of the reference light by discontinuous values.

The device of Patent Document 1 uses a technique of so-called "Fourier Domain OCT." That is to say, the device irradiates a low coherence light beam to an object, superposes the reflected light and the reference light to generate an interference light, and acquires the spectral intensity distribution of the interference light to execute Fourier transform, thereby imaging the morphology in the depth direction (the z-direction) of the object. The technique of this type is also called Spectral Domain.

Furthermore, the device described in Patent Document 1 is provided with a Galvano mirror that scans with a light beam (a signal light), and is thereby configured to form an image of a desired measurement target region of the object. Because this device is configured to scan with the light beam only in one direction (the x-direction) orthogonal to the z-direction, an image formed by this device is a two-dimensional tomographic image in the depth direction (the z-direction) along the scanning direction (the x-direction) of the light beam.

Patent Document 2 discloses a technique of scanning with a signal light in the horizontal direction (x-direction) and the vertical direction (y-direction) to form a plurality of two-dimensional tomographic images in the horizontal direction, and acquiring and imaging three-dimensional tomographic information of a measured range based on the tomographic images. As the three-dimensional imaging, for example, a method of arranging and displaying a plurality of tomographic images in the vertical direction (referred to as stack data or the like), and a method of executing a rendering process on a plurality of tomographic images to form a three-dimensional image are considered.

Patent Documents 3 and 4 disclose other types of OCT devices. Patent Document 3 describes an OCT device that images the morphology of an object by sweeping the wavelength of light that is irradiated to an object, acquiring the spectral intensity distribution based on an interference light obtained by superposing the reflected lights of the light of the respective wavelengths on the reference light, and executing Fourier transform. Such an OCT device is called a Swept Source type or the like. The Swept Source type is a kind of the Fourier Domain type.

Further, Patent Document 4 describes an OCT device that irradiates a light having a predetermined beam diameter to an object and analyzes the components of an interference light obtained by superposing the reflected light and the reference light, thereby forming an image of the object in a cross-section orthogonal to the travelling direction of the light. Such an OCT device is called a full-field type, en-face type or the like.

Patent Document 5 discloses a configuration in which the OCT is applied to the ophthalmologic field. Before the OCT device was applied to the ophthalmologic field, an ophthalmic observation apparatus such as a retinal camera and a slit lamp had been used (for example, refer to Patent Document 6 and Patent Document 7). A fundus camera is a device that irradiates the subject eye with illuminating light and receives light reflected from the fundus to capture an image of the fundus. A slit lamp is a device that acquires an image of the cross-section of the cornea by cutting off an optical section of the cornea using slit light.

An ophthalmic observation apparatus using OCT is advantageous compared to conventional ophthalmic imaging devices with respect to the fact that it is capable of acquiring high-definition images, and is also capable of acquiring tomographic images and three-dimensional images.

In this way, because the ophthalmic observation apparatus using OCT may be applied to observations of various portions of a subject eye and is capable of acquiring high-definition images, it is being applied to the diagnosis of various ophthalmic disorders.

PRIOR ART DOCUMENTS

Patent Documents

[Patent Document 1]
Japanese Unexamined Patent Application Publication No. Hei 11-325849
[Patent Document 2]
Japanese Unexamined Patent Application Publication No. 2002-139421
[Patent Document 3]
Japanese Unexamined Patent Application Publication No. 2007-24677
[Patent Document 4]
Japanese Unexamined Patent Application Publication No. 2006-153838
[Patent Document 5]
Japanese Unexamined Patent Application Publication No. 2008-73099
[Patent Document 6]
Japanese Unexamined Patent Application Publication No. Hei 9-276232
[Patent Document 7]
Japanese Unexamined Patent Application Publication No. 2008-259544

DISCLOSURE OF THE INVENTION

Problem that the Invention is to Solve

However, its use in the diagnosis of various disorders causes the need to perform examinations of various portions of a subject eye under various setting conditions. For example, for the diagnosis of one disorder, it is necessary to perform a prescribed analytic process on a three-dimensional image of the area near the macula of the fundus, while for the diagnosis of another disorder, it is necessary to acquire concentric images of the area surrounding the optic papilla and perform a different analytic process. Furthermore, setting items for examinations include the imaged portion, the scanning method, the image analysis method, and display layout, and the printing layout, etc.

In a conventional device, operations for setting various items such as those described above are performed manually by an operator. If the settings are appropriate, the information required for diagnosis can be handled without excess or deficiency, but settings are not always implemented appropriately. For example, if the operator is unfamiliar with the device or does not have a good knowledge of the disorder, there is a concern that they may be unsure of how to combine the above setting items to acquire the information required for diagnosis, or may be unable to make a determination.

If the above items are set in this way based on determinations made by the operator, there may be problems such as a failure to acquire the information required for diagnosis, or the acquisition of unnecessary information. This creates a concern that diagnosis may not be performed appropriately. Moreover, time and effort will be wasted repeating the examination or sorting out necessary information and unnecessary information.

Furthermore, even if one is proficient in setting operations, it takes effort and time to set multiple items each time.

The present invention has been devised to resolve the above problems, and the purpose is to provide an ophthalmic observation apparatus capable of acquiring information used for the diagnosis of a subject eye easily and without excess or deficiency.

Means for Solving the Problem

In order to achieve the aforementioned objects, ophthalmic observation apparatus comprises: an optical system that divides low-coherence light into a signal light and a reference light, overlaps said signal light that has passed through a subject eye and the reference light that has passed through a reference light path, and generates and detects interference light; an image forming means that, based on the detection results of said interference light by said optical system, forms an image of said subject eye; an analysis means that analyzes said formed image; an output means that outputs examination-results information including the image analysis results by said analysis means; a storage means that preliminarily stores operation mode information in which each of a plurality of operation modes corresponding to examination types is associated with the operational details of at least one of said optical system, said image forming means, said analysis means, and said output means; a designating means that designates one of said plurality of operation modes; and a control means that refers to the operation mode information stored in said storage to identify the operational details associated with said designated operation mode, and controls said optical system, said image forming means, said analysis means, and/or said output means based on said identified operational details.

The optical system can include a fixation optical system that present said subject eye with a fixation target for fixating said subject eye in a prescribed fixation direction, in said operation mode information, fixation directions by said fixation optical system are associated with each of said plurality of operation modes, and said control means refers to said operation mode information to identify the fixation direction associated with said designated operation mode, and also controls said fixation optical system to present said fixation target for fixating in the identified fixation direction.

The fixation optical system can include a display device that displays said fixation target, and a projection optical system that projects said displayed fixation target to said subject eye, in said operation mode information, display positions of said fixation target on said display device are associated as the fixation directions for each of said plurality of operation modes, and said control means refers to said operation mode information to identify the display position associated with said designated operation mode, and also controls said display device to display said fixation target at the identified display position on said display device.

The optical system can include a scanning means that scans the irradiation position of said signal light on said subject eye, in said operation mode information, each of said plurality of operation modes is associated with a scanning pattern of said irradiation position by said scanning means, and with an image type formed by said image forming means, and said control means refers to said operation mode information to identify the scanning pattern and image type associated with said designated operation mode, and also controls said scanning means to scan the irradiation position of said signal light in the identified scanning pattern, and controls said image forming means to form an image of said subject eye of the identified image type.

The analysis means is capable of executing a plurality of sets of analytic processing, including layer-thickness analysis that obtains the thickness of a prescribed layer of said subject eye, and lesion identification analysis that identifies the position of a lesion in said subject eye, in said operation mode information, each of said plurality of operation modes is associated with at least one of said plurality of sets of analytic processing, and said control means refers to said operation mode information to identify the analytic processing associated with said designated operation mode, and also controls said analysis means to execute the identified analytic processing.

Further, in said operation mode information, each of said plurality of operation modes is associated with an information type included in said examination-results information, and with an output layout of said examination-results information by said output means, and said control means refers to said operation mode information to identify the information type and output layout associated with said designated operation mode, and also controls said output means to arrange and output said examination-results information including the identified information type in the identified output layout.

Another ophthalmic observation apparatus can comprise: an optical system including: a fixation optical system that presents a subject eye with a fixation target for fixating said subject eye in a prescribed fixation direction; a dividing means that divides low-coherence light into a signal light and a reference light; a scanning means that scans the irradiation position of said signal light on said subject eye; an overlapping means that overlaps said signal light that has passed through said subject eye and the reference light that has passed through a reference light path to generate interference light; and a detection means that detects said generated interference light; an image forming means that forms an image of said subject eye based on the detection results of said interference light by said detection means; an analysis means that is capable of executing a plurality of sets of analytic processing, including layer-thickness analysis that analyzes said formed image to obtain the thickness of a prescribed layer of said subject eye, and lesion identification analysis that analyzes said formed image to identify the position of a lesion in said subject eye; an output means that outputs examination-results information including the image analysis results from said analysis means; a storage means that preliminarily stores operation mode information in which each of a plurality of operation modes corresponding to examination types is associated with a fixation direction by said fixation optical system, a scanning pattern of said irradiation position by said scanning means, an image type formed by said image forming means, at least one of said plurality of sets of analytic processing, an information type included in said examination-results information, and an output layout of said examination-results information from said output means; a designating means that designates one of said plurality of operation modes; and a control means refers to said operation mode information to identify the fixation direction, scanning pattern, image type, analytic processing, information type, and output layout associated with said designated operation mode, and also controls said fixation optical system to present said fixation target for fixating in the identified fixation direction, controls said scanning means to scan the irradiation position of said signal light in the identified scanning pattern, controls said image forming means to form an image of said subject eye of the identified image type, controls said analysis means to execute the identified analytic processing, and controls said output means to arrange and output said examination-results information including the identified information type in the identified output layout.

In said another ophthalmic observation apparatus said plurality of operation modes can include a macular examination mode for examining the macula of the fundus, and in said operation mode information, in relation to said macular examination mode: a macula fixation direction for irradiating the macula and the surrounding area with said signal light is associated as said fixation direction; a three-dimensional scan that sequentially irradiates said signal light on a plurality of irradiation positions arranged in the form of lattice points, a radial scan that sequentially irradiates said signal light on a plurality of irradiation positions arranged radially, or a line scan that sequentially irradiates said signal light on a plurality of irradiation positions arranged linearly is associated as said scanning pattern; as said image type, a three-dimensional image is associated if said scanning pattern is said three-dimensional scan, or a tomographic image is associated if said scanning pattern is said radial scan or said line scan; a retinal thickness analysis that obtains the retinal thickness and compares it with a prescribed standard thickness is associated as said analytic processing; a tomographic image and the results of said comparison by said retinal thickness analysis are associated as said information type; and a macular examination template that arranges said tomographic image and the results of said comparison in a prescribed arrangement is associated as said output layout.

In said another ophthalmic observation apparatus said plurality of operation modes can include an optic-disc examination mode for examining the optic papilla of the fundus, and in said operation mode information, in relation to said optic-disc examination mode: an optic-disc fixation direction for irradiating the optic papilla and the surrounding area with said signal light is associated as said fixation direction; a circle scan that sequentially irradiates said signal light on a plurality of irradiation positions arranged circularly, or a three-dimensional scan that sequentially irradiates said signal light on a plurality of irradiation positions arranged in the form of lattice points is associated as said scanning pattern; as said image type, a tomographic image is associated if said scanning pattern is said circle scan, or a three-dimensional image is associated if said scanning pattern is said three-dimensional scan; an RNFL (retinal nerve fiber layer) thickness analysis that obtains the RNFL thickness and compares it with a prescribed standard thickness, and an optic-disc shape analysis that detects the opening of the retina and analyzes the shape of the optic papilla are associated as said analytic processing; a tomographic image, the results of said comparison from said RNFL thickness analysis, and the results of said optic-disc shape analysis are associated as said information type; and an optic-disc examination template that arranges said tomographic image, the results of said comparison, and the results of said optic-disc shape analysis in a prescribed arrangement is associated as said output layout.

In said another ophthalmic observation apparatus said plurality of operation modes can include a glaucoma examination mode for performing glaucoma examinations, and in said operation mode information, in relation to said glaucoma examination mode: a macular fixation direction for irradiating the macula and the surrounding area with said signal light, and an optic-disc fixation direction for irradiating the optic papilla and the surrounding area with said signal light are associated as said fixation direction; a three-dimensional scan that sequentially irradiates said signal light on a plurality of irradiation positions arranged in the form of lattice points is associated as said scanning pattern; a three-dimensional image of the macula and the surrounding area and a three-dimensional image of the optic papilla and the surrounding area are associated as said image type; an RNFL (retinal nerve fiber layer) thickness analysis that obtains the RNFL thickness and compares it with a prescribed standard thickness, and an optic-disc shape analysis that detects the opening of the retina and analyzes the shape of the optic papilla are associated as said analytic processing; a tomographic image, the results of said comparison from said RNFL thickness analysis, and the results of said optic-disc shape analysis are associated as said information type; and a glaucoma diagnosis template that arranges said tomographic image, the results of said comparison, and the results of said optic-disc shape analysis in a prescribed arrangement is associated as said output layout.

In said another ophthalmic observation apparatus said plurality of operation modes can include a macular-degeneration examination mode for performing macular-degeneration examinations, and in said operation mode information, in relation to said macular-degeneration examination mode: a macula fixation direction for irradiating the macula and the surrounding area with said signal light is associated as said fixation direction; a three-dimensional scan that sequentially irradiates said signal light on a plurality of irradiation positions arranged in the form of lattice points is associated as said scanning pattern; a three-dimensional image of the macula and the surrounding area is associated as said image type; a retinal thickness analysis that obtains the retinal thickness and compares it with a prescribed standard thickness, and a drusen analysis that obtains the distribution of drusen are associated as said analytic processing; a tomographic image, the results of said retinal thickness analysis, and the results of said drusen analysis are associated as said information type; and a macular-degeneration diagnosis template that arranges said tomographic image, the results of said retinal thickness analysis, and the results of said drusen analysis in a prescribed arrangement is associated as said output layout.

The ophthalmic observation apparatus can comprise: an input means that inputs patient identification information, wherein said control means stores the operation mode for each examination in said storage means together with said input patient identification information, when patient identification information is input by said input means, said designating means retrieves the operation mode stored together with this patient identification information in the past from said storage means, and said control means controls said optical system, said image forming means, said analysis means, and/or said output means based on the operational details associated with said retrieved operation mode.

Said another ophthalmic observation apparatus can comprise: an input means that inputs patient identification information, wherein said control means the operation mode for each examination in said storage means together with said input patient identification information, when patient identification information is input by said input means, said designating means retrieves the operation mode stored together with this patient identification information in the past from said storage means, and said control means controls said optical system, said image forming means, said analysis means, and/or said output means based on the operational details associated with said retrieved operation mode.

The ophthalmic observation apparatus can comprise: an input means that inputs patient identification information, and a timekeeping means that keeps the current date and time, wherein in said operation mode information, said operation mode is associated with an examination interval representing the time interval for performing examinations in the operation mode, said control means stores the operation mode for each examination in said storage means together with said input patient identification information and said kept date and time, when patient identification information is input by said input means, said designating means retrieves the operation mode and date and time stored together with this patient identification information in the past from said storage means, calculates the difference between said retrieved past date and time with the current date and time being kept by said timekeeping means to obtain the examination interval, and selects the operation mode associated with said obtained examination interval from among said plurality of operation modes, and said control means controls said optical system, said image forming means, said analysis means, and/or said output means based on the operational details associated with said selected operation mode.

Said another ophthalmic observation apparatus can comprise: an input means that inputs patient identification information, and a timekeeping means that keeps the current date and time, wherein in said operation mode information, said operation mode is associated with an examination interval representing the time interval for performing examinations in the operation mode, said control means stores the operation mode for each examination in said storage means together with said input patient identification information and said kept date and time, when patient identification information is input by said input means, said designating means retrieves the operation mode and date and time stored together with this patient identification information in the past from said storage means, calculates the difference between said retrieved past date and time with the current date and time being kept by said timekeeping means to obtain the examination interval, and selects the operation mode associated with said obtained examination interval from among said plurality of operation modes, and said control means controls said optical system, said image forming means, said analysis means, and/or said output means based on the operational details associated with said selected operation mode.

The ophthalmic observation apparatus can comprise: an input means that inputs patient identification information, wherein if an abnormality is present in the analysis results obtained by said analysis means, said control means stores abnormal-presence information indicating as such in said storage means together with said input patient identification information, in said operation mode information, said operation mode is associated with operational-change information representing changes to the operational details if said abnormality is present, when patient identification information is input by said input means, said designating means retrieves abnormal-presence information stored together with this patient identification information in the past from said storage means, and if said abnormal-presence information is retrieved, changes the operational details of said operation mode based on said operational-change information, and said control means controls said optical system, said image forming means, said analysis means, and/or said output means based on the operational details after said change.

Said another ophthalmic observation apparatus can comprise: an input means that inputs patient identification information, wherein if an abnormality is present in the analysis results obtained by said analysis means, said control means stores abnormal-presence information indicating as such in said storage means together with said input patient identification information, in said operation mode information, said operation mode is associated with operational-change information representing changes to the operational details if said abnormality is present, when patient identification information is input by said input means, said designating means retrieves abnormal-presence information stored together with this patient identification information in the past from said storage means, and if said abnormal-presence information is retrieved, changes the operational details of said operation mode based on said operational-change information, and said control means controls said optical system, said image forming means, said analysis means, and/or said output means based on the operational details after said change.

The ophthalmic observation apparatus can comprise: an image-capturing means that irradiates the fundus of the subject eye with illuminating light and receives light reflected from the fundus from this illuminating light to form a captured image of said fundus, wherein in said operation mode information, at least one of said plurality of operation modes is associated with the operational details of said image-capturing means, and if the operational details of said image-capturing means are associated with the operation mode designated by said designating means, said control means controls said image-capturing means based on the operational details to form a captured image of said fundus.

Said another ophthalmic observation apparatus can comprise: an image-capturing means that irradiates the fundus of the subject eye with illuminating light and receives light reflected from the fundus from this illuminating light to form a captured image of said fundus, wherein in said operation mode information, at least one of said plurality of operation modes is associated with the operational details of said image-capturing means, and if the operational details of said image-capturing means are associated with the operation mode designated by said designating means, said control means controls said image-capturing means based on the operational details to form a captured image of said fundus.

The ophthalmic observation apparatus can comprise: an operation means that is used for editing the operational details associated with said operation mode according to said operation mode information.

Said another ophthalmic observation apparatus can comprise: an operation means that is used for editing the operational details associated with said operation mode according to said operation mode information.

Effect of the Invention

The ophthalmic observation apparatus according to the present invention is capable of selectively executing multiple operation modes, and preliminarily stores operation mode information that associates each operation mode with operational details. When one operation mode is designated, the ophthalmic observation apparatus refers to the operation mode information to identify the operational details associated with this operation mode, and controls the optical system, the image forming means, the analysis means, and/or the output means based on the identified operational details.

According to this type of ophthalmic observation apparatus, it is possible to automatically execute a series of processes corresponding to a designated operation mode, and it is therefore possible to acquire information used for diagnosing the subject eye easily and without excess or deficiency.

BRIEF DESCRIPTION OF THE DRAWINGS

FIG. 4 is a schematic block diagram showing an example of a configuration of an embodiment of an ophthalmic observation apparatus according to the present invention.

FIG. 5 is table information showing the outline of an example of operation mode information of an embodiment of an ophthalmic observation apparatus according to the present invention.

MODE FOR CARRYING OUT THE INVENTION

An example of an embodiment of an ophthalmic observation apparatus according to the present invention will be described in detail with reference to the drawings.

The ophthalmic observation apparatus according to the present invention forms tomographic images and three-dimensional images of a subject eye using optical coherence tomography. Optical coherence tomography of an arbitrary type is applicable to the ophthalmic observation apparatus. Note that when a configuration involving scanning with a signal light is used, Fourier Domain type or swept source type, etc. is applied. Below, an image obtained by optical coherence tomography may be referred to as an OCT image. Furthermore, a measuring action for forming an OCT image is sometimes referred to as an OCT measurement.

In the following embodiments, an ophthalmic observation apparatus to which a Fourier-Domain-type is applied in order to perform the OCT measurement of a fundus will be described in detail. To be specific, in these embodiments, similar to a device disclosed in Patent Document 5, an ophthalmic observation apparatus that is capable of performing both the OCT measurement of a fundus and fundus photographing will be picked up.

It should be noted that the ophthalmic observation apparatus according to the present invention is not limited to use for fundus examinations, and may be a device for examining other portions of a subject eye (e.g., the cornea, the lens, the vitreous body, etc.).

[Configuration]

Figure 1:
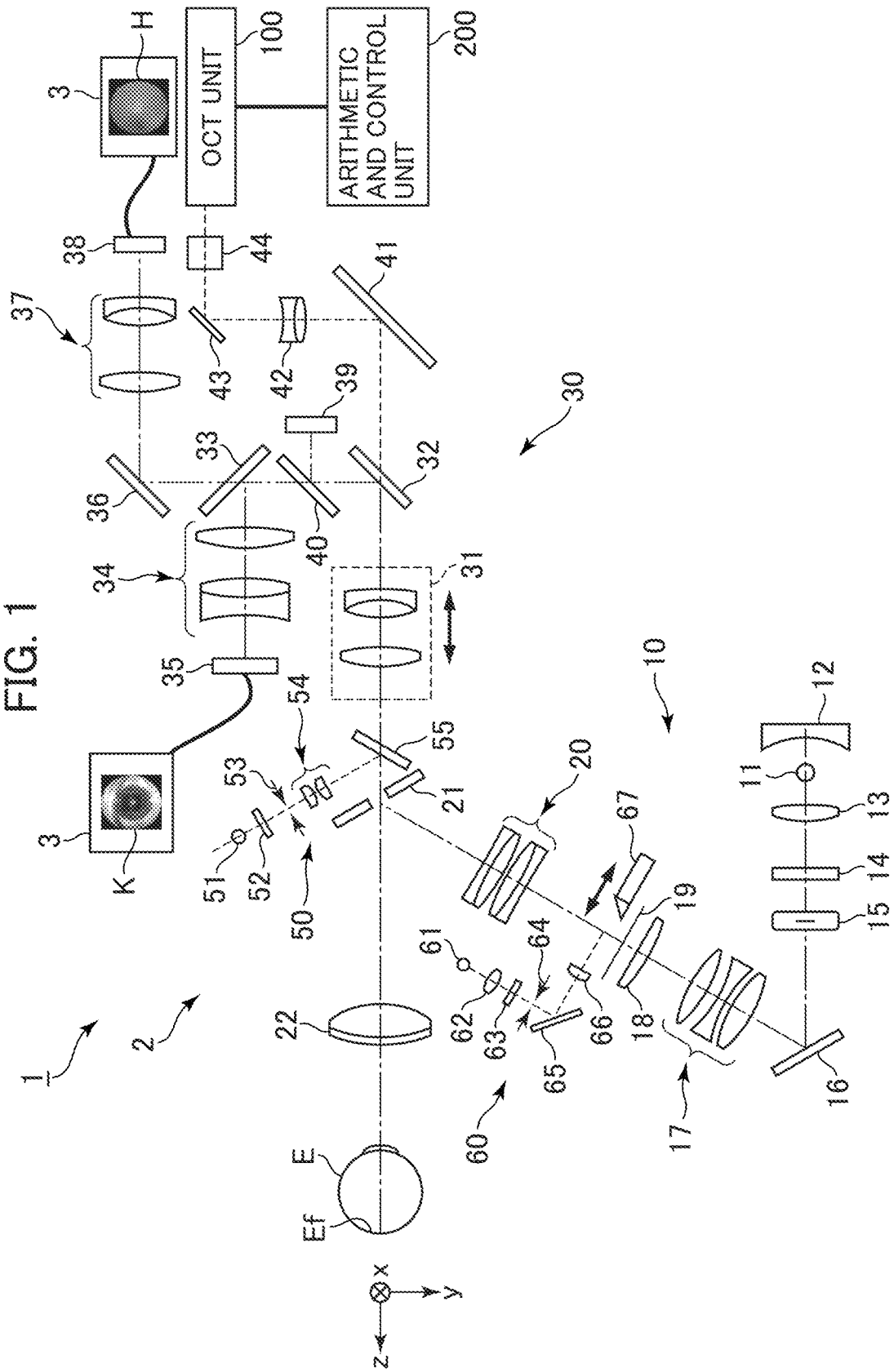
FIG. 1 is a schematic view showing an example of a configuration of an embodiment of an ophthalmic observation apparatus according to the present invention.
Figure 2:
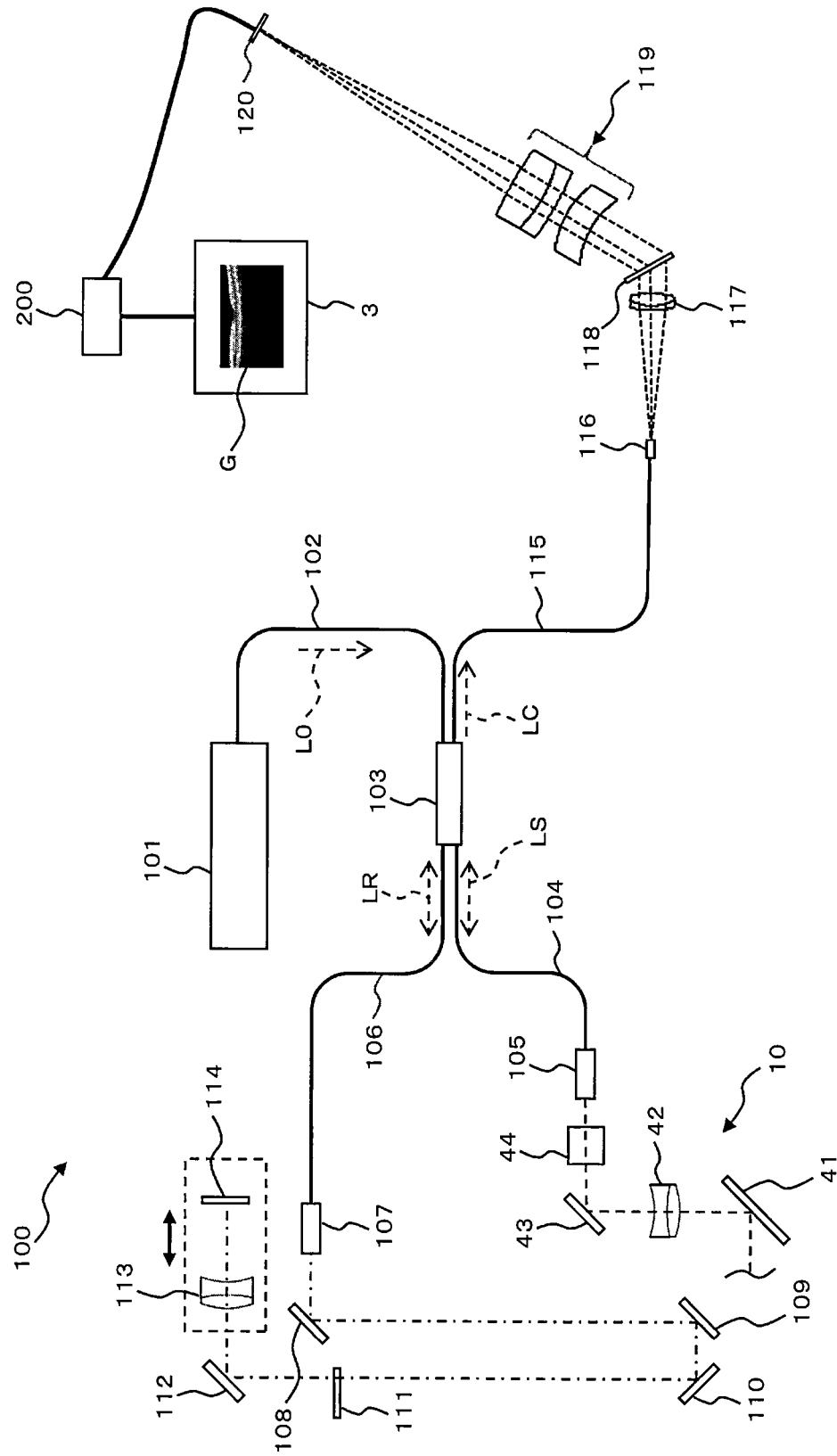
FIG. 2 is a schematic view showing an example of a configuration of an embodiment of an ophthalmic observation apparatus according to the present invention.

An ophthalmic observation apparatus 1, as shown in FIG. 1 and FIG. 2, includes a retinal camera unit 2, an OCT unit 100, and an arithmetic and control unit 200. The retinal camera unit 2 has almost the same optical system as a conventional retinal camera. The OCT unit 100 is provided with an optical system for obtaining an OCT image of a fundus. The arithmetic and control unit 200 is provided with a computer that executes various arithmetic processes, control processes, and so on.

[Retinal Camera Unit]

The retinal camera unit shown in FIG. 1 is provided with an optical system for forming a 2-dimensional image (fundus image) representing the surface morphology of the fundus Ef of an eye E. Fundus images include observation images, captured images, etc. The observation image is, for example, a monochrome moving image formed at a prescribed frame rate using near-infrared light. The captured image is, for example, a color image captured by flashing visible light. Furthermore, captured images include fluorescent images such as a fluorescein angiography image or an indocyanine green fluorescent image.

The retinal camera unit 2 is provided with a chin rest and a forehead placement for retaining the face of the subject, similar to a conventional retinal camera. Moreover, like a conventional retinal camera, the retinal camera unit 2 is provided with an illumination optical system 10 and an imaging optical system 30. The illumination optical system 10 irradiates an illumination light to the fundus Ef. The imaging optical system 30 guides a fundus reflected light of the illumination light to imaging devices (CCD image sensors 35, 38). Moreover, the imaging optical system 30 guides a signal light coming from the OCT unit 100 to the fundus Ef, and guides the signal light propagated through the fundus Ef to the OCT unit 100. The illumination optical system 10 and the imaging optical system 30 are an example of an "image-capturing means" of the present invention.

An observation light source 11 of the illumination optical system 10 comprises, for example, a halogen lamp. Light (observation illumination light) output from the observation light source 11 is reflected by a reflection mirror 12 with a curved reflection surface, and becomes near infrared after passing through a visible cut filter 14 via a condenser lens 13. Furthermore, the observation illumination light is once converged near an imaging light source 15, reflected by a mirror 16, and passes through relay lenses 17, 18, diaphragm 19, and relay lens 20. Then, the observation illumination light is reflected on the peripheral part (the surrounding region of an aperture part) of an aperture mirror 21 and illuminates the fundus Ef via an object lens 22.

The fundus reflection light of the observation illumination light is refracted by the object lens 22, passes through the aperture part formed in the center region of the aperture mirror 21, passes through a dichroic mirror 55 and, travels through a focusing lens 31, and is reflected by a dichroic mirror 32. Furthermore, the fundus reflection light passes through a half-mirror 40 and forms an image on the light receiving surface of the CCD image sensor 35 by a condenser lens 34 after being reflected by a dichroic mirror 33. The CCD image sensor 35 detects, for example, the fundus reflection light at a prescribed frame rate. An image (observation image)

K based on the fundus reflection light detected by the CCD image sensor 35 is displayed on a display device 3.

The imaging light source 15 consists of, for example, a xenon lamp. The light (imaging illumination light) output from the imaging light source 15 is irradiated to the fundus Ef via a route that is similar to the observation illumination light. The fundus reflection light of the imaging illumination light is guided to the dichroic mirror 33 via the same route as that of the observation illumination light, passes through the dichroic mirror 33, and forms an image on the light receiving surface of the CCD image sensor 38 by a condenser lens 37 after being reflected by a mirror 36. An image (captured image) H based on the fundus reflection light detected by the CCD image sensor 38 is displayed on the display device 3. It should be noted that the display device 3 for displaying an observation image K and the display device 3 for displaying a captured image H may be the same or different.

An LCD (Liquid Crystal Display) 39 displays a fixation target or a visual target for measuring eyesight. The fixation target is a visual target for fixing the eye E, and is used when photographing a fundus or forming a tomographic image.

Part of the light output from the LCD 39 is reflected by a half-mirror 40, reflected by the dichroic mirror 32, passes through the aperture part of the aperture mirror 21 via the focusing lens 31 as well as a dichroic mirror 55, is refracted by the object lens 22 and projected to the fundus Ef.

By changing a display position of the fixation target on the screen of the LCD 140, it is possible to change a fixation direction (also referred to as a fixation position) of the eye E. As the fixation direction of the eye E, there are a direction for acquiring an image centered on the macula of the fundus Ef (macula fixation direction), a direction for acquiring an image centered on the optic papilla (optic-disc fixation direction), a direction for acquiring an image centered on the fundus center between the macula and the optic papilla (fundus center fixation direction), and so on, for example, as in conventional retinal cameras.

The LCD 39 is one example of the "display device" of the present invention. The above optical element group that projects the fixation target displayed on the LCD 39 to the fundus Ef configures one example of the "projection optical system" of the present invention. Moreover, the LCD 39 and the above optical element group configure one example of the "fixation optical system" of the present invention.

Furthermore, as with conventional fundus cameras, the retinal camera unit 2 is provided with an alignment optical system 50 and a focus optical system 60. The alignment optical system 50 generates a target (alignment target) for matching the position (alignment) of the device optical system with respect to the eye E. The focus optical system 60 generates a target (split target) for matching the focus with respect to the eye Ef.

Light (alignment light) output from the LED (Light Emitting Diode) 51 of the alignment optical system 50 is reflected by the dichroic mirror 55 via diaphragms 52, 53 and a relay lens 54, passes through the aperture part of the aperture mirror 21, and is projected onto the cornea of the eye E by the object lens 22.

Part of cornea reflection light of the alignment light is transmitted through the dichroic mirror 55 via the object lens 22 and the aperture part, passes through the focusing lens 31, is reflected by the dichroic mirror 32, transmitted through the half-mirror 40, reflected by the dichroic mirror 33, and projected onto the light receiving surface of the CCD image sensor 35 by the condenser lens 34. An image (alignment target) captured by the CCD image sensor 35 is displayed on the display device 3 along with the observation image K. A user conducts alignment by an operation that is the same as conventional fundus cameras. It should be noted that alignment may be performed, by an arithmetic and control unit 200, as a result of analyzing the position of the alignment target and moving the optical system.

In order to conduct focus adjustment, the reflection surface of a reflection rod 67 is provided in a slanted position on the light path of the illumination optical system 10. Light (focus light) output from an LED 61 of the focus optical system 60 passes through a relay lens 62, is split into two light fluxes by a split target plate 63, passes through a two-hole diaphragm 64, is reflected by a mirror 65, and is reflected after an image is formed once on the reflection surface of the reflection rod 67 by a condenser lens 66. Furthermore, the focus light is reflected at the aperture mirror 21 via the relay lens 20 and an image is formed on the fundus Ef by the object lens 22.

The fundus reflection light of the focus light passes through the same route as the cornea reflection light of the alignment light and is detected by the CCD image sensor 35. A light (split target) captured by the CCD image sensor 35 is displayed on the display device 3 along with an observation image K. The arithmetic and control unit 200, as in the past, analyzes the position of the split target, and moves the focusing lens 31 and the focus optical system 60 for focusing. It should be noted that focusing may be performed manually while visually recognizing the split target.

An optical path including a mirror 41, collimator lens 42, and Galvano mirrors 43, 44 is provided behind the dichroic mirror 32. The optical path is guided to the OCT unit 100.

The Galvano mirror 44 performs scanning with a signal light LS from the OCT unit 100 in the x-direction. The Galvano mirror 43 performs scanning with a signal light LS in the y-direction. Scanning may be performed with the signal light LS in an arbitrary direction in the xy-plane due to the two Galvano mirrors 43 and 44. As a result, it is possible to scan the irradiation position of the signal light LS with respect to the fundus Ef.

[OCT Unit]

The OCT unit 100 is provided with an optical system for obtaining a tomographic image of the fundus Ef (see FIG. 2). The optical system has a similar configuration to a conventional Fourier-Domain-type OCT device. That is to say, the optical system is configured to split a low coherence light into a reference light and a signal light, make the signal light propagated through a fundus and the reference light propagated through a reference optical path interfere with each other to generate an interference light, and detects the spectral components of this interference light. This detection result (detection signal) is transmitted to the arithmetic and control unit 200.

The optical element group housed in the OCT unit 100 as well as the optical element group on the light path of the signal light that is housed in the retinal camera unit 2 configure one example of the "optical system" of the present invention.

The light source unit 101 outputs a broadband, low-coherence light L0. The low-coherence light L0 includes, for example, a near-infrared waveband (approximately 800 nm to 900 nm), and has a temporal coherence length of around several tens of micrometers. Furthermore, a waveband that is not visible to the human eye, such as near-infrared light with a central wavelength of around 1050 to 1060 nm, for example, may be used as the low-coherence light L0.

A light source unit 101 outputs a low coherence light L0. The low coherence light L0 is, for example, light (invisible light) consisting of wavelengths that is impossible to be detected by human eyes. Furthermore, the low coherence light L0 is, for example, near-infrared light having the center wavelength of about 1050-1060 nm. The light source unit 101 is configured to include light output device, such as an SLD (super luminescent diode), LED, SOA (Semiconductor Optical Amplifier) and the like. A light source unit 101 is an example of a "light source" of the invention.

The low coherence light L0 output from the light source unit 101 is guided to a fiber coupler 103 by an optical fiber 102 and split into signal light LS and reference light LR. It should be noted that the fiber coupler 103 acts both as a means to split light (splitter) as well as a means to synthesize light (coupler), but herein the same is conventionally referred to as a "fiber coupler."

The signal light LS is guided by the optical fiber 104 and becomes a parallel light flux by a collimator lens unit 105. Furthermore, the signal light LS is reflected by Galvano mirrors 44 and 43, converged by the collimator lens 42, reflected by the mirror 41, transmitted through a dichroic mirror 32, and irradiated to the fundus Ef after passing through a route that is the same as the light from the LCD 39. The signal light LS is scattered and reflected at the fundus Ef. The scattered light and the reflection light are sometimes all together referred to as the fundus reflection light of the signal light LS. The fundus reflection light of the signal light LS progresses along the same route in the reverse direction and is guided to the fiber coupler 103.

The reference light LR is guided by an optical fiber 106 and becomes a parallel light flux by a collimator lens unit 107. Furthermore, the reference light LR is reflected by mirrors 108, 109, 110, dimmed by an ND (Neutral Density) filter 111, and reflected by a mirror 112, with the image formed on a reflection surface of a reference mirror 114 by a collimator lens 113. The reference light LR reflected by the reference mirror 114 progresses along the same route in the reverse direction and is guided to the fiber coupler 103. It should be noted that an optical element for dispersion compensation (pair prism, etc.) and/or an optical element for polarization correction (wave plate, etc.) may also be provided for the optical path (reference optical path) of the reference light LR.

The fiber coupler 103 superposes the fundus reflection light of the signal light LS and the reference light LR reflected by the reference mirror 114. Interference light LC thus generated is guided by an optical fiber 115 and output from an exit end 116. Furthermore, the interference light LC is converted to a parallel light flux by a collimator lens 117, spectrally divided (spectrally decomposed) by a diffraction grating 118, converged by the convergence lens 119, and projected onto the light receiving surface of a CCD image sensor 120. Although the diffraction grating 118 shown in FIG. 2 is of the transmission type, it is possible to use the reflection type.

The CCD image sensor 120 is for example a line sensor, and detects the respective spectral components of the spectrally decomposed interference light LC and converts the components into electric charges. The CCD image sensor 120 accumulates these electric charges and generates a detection signal. Furthermore, the CCD image sensor 120 transmits the detection signal to the arithmetic and control unit 200.

Although a Michelson-type interferometer is employed in this embodiment, it is possible to employ any type of interferometer such as a Mach-Zehnder-type as necessary. Instead of a CCD image sensor, other types of image sensors, such as a CMOS (Complementary Metal Oxide Semiconductor) image sensor, can be used.

[Arithmetic and Control Unit]

A configuration of the arithmetic and control unit 200 will be described. The arithmetic and control unit 200 analyzes the detection signals inputted from the CCD image sensor 120, and forms an OCT image of the fundus Ef. An arithmetic process for this is the same as that of a conventional Fourier-Domain-type OCT device.

Further, the arithmetic and control unit 200 controls each part of the retinal camera unit 2, the display device 3 and the OCT unit 100. For example, the arithmetic and control unit 200 causes the display device 3 to display a tomographic image G of the fundus Ef (see FIG. 2).

Moreover, as control of the retinal camera unit 2, the arithmetic and control unit 200 executes: control of action of the observation light source 101, the imaging light source 103 and LED's 51 and 61; control of action of the LCD 39; control of movement of the focusing lens 31; control of movement of the reflection rod 67; control of movement of the focus optical system 60; control of action of the respective Galvano mirrors 43 and 44; and so on.

Further, as control of the OCT unit 100, the arithmetic and control unit 200 executes: control of action of the light source unit 101; control of movement of the reference mirror 114 and the collimator lens 113; control of action of the CCD image sensor 120; and so on.

The arithmetic and control unit 200 includes a microprocessor, a RAM, a ROM, a hard disk drive, a communication interface, and so on, as in conventional computers. The storage device such as the hard disk drive stores a computer program for controlling the ophthalmic observation apparatus 1. The arithmetic and control unit 200 may be provided with a circuit board dedicated for forming OCT images based on detection signals from the CCD image sensor 120. Moreover, the arithmetic and control unit 200 may be provided with operation devices (input devices) such as a keyboard and a mouse, and/or display devices such as LCD.

The retinal camera unit 2, display device 3, OCT unit 100, and arithmetic and control unit 200 may be integrally configured (that is, within a single case), or configured as separate bodies.

[Control System]

Figure 3:
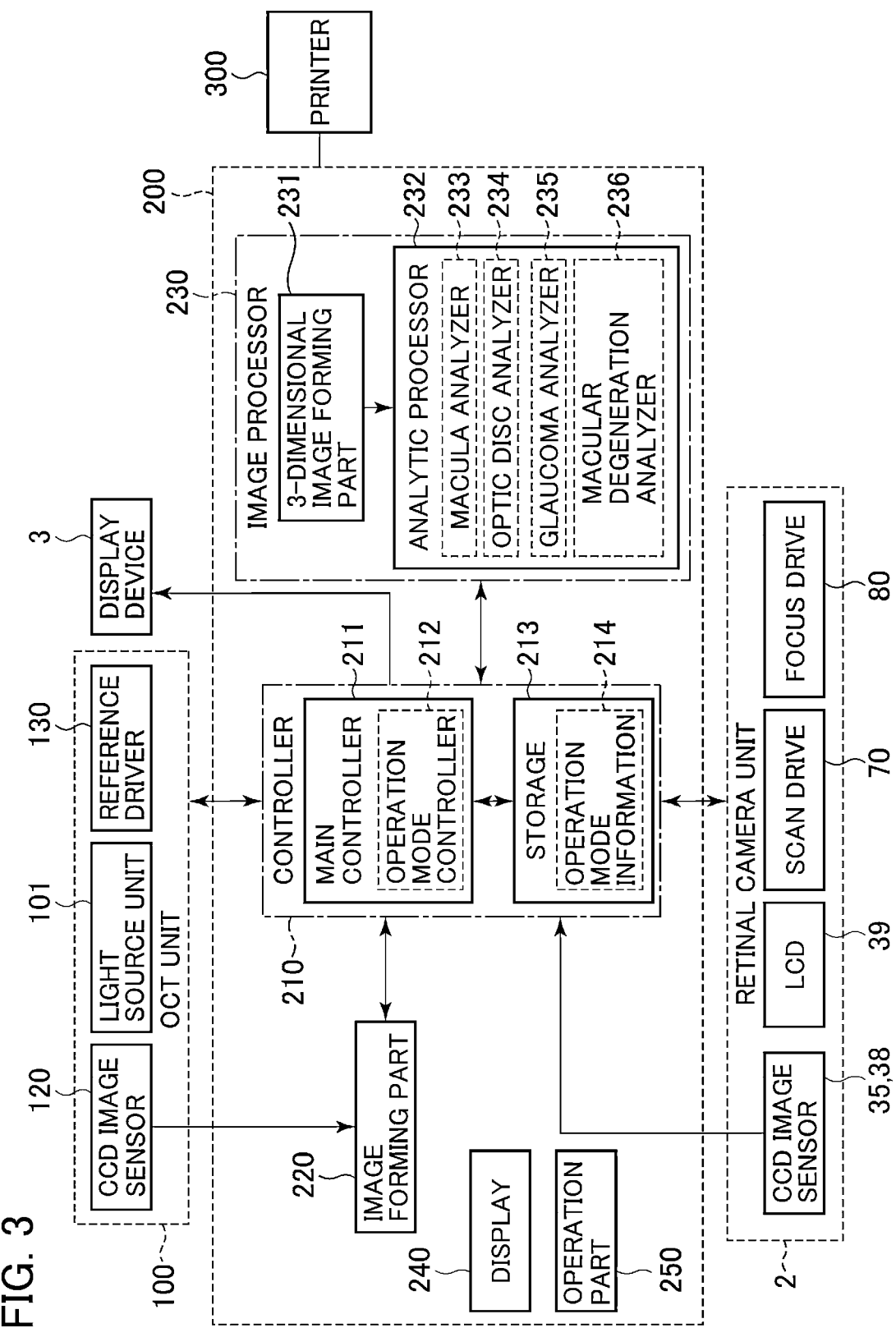
FIG. 3 is a schematic block diagram showing an example of a configuration of an embodiment of an ophthalmic observation apparatus according to the present invention.

A configuration of a control system of the ophthalmic observation apparatus 1 will be described with reference to FIG. 3 and FIG. 4.

The ophthalmic observation apparatus 1 selectively executes multiple operation modes. An operation mode combines various operation items of the ophthalmic observation apparatus 1 and executes them as a series of operations, and is also referred to as a macro function. Operation items include the display position of a fixation target (i.e., the fixation direction of the subject eye E), the scanning pattern of the signal light LS, the type of image formed (tomographic image, three-dimensional image, etc.), the type of analytic process, the type of information output as examination results (examination-results information), and the output layout of examination-results information, etc. The ophthalmic observation apparatus 1 executes each operation mode by combining the choices for each operation item.

A printer 300 is connected to the arithmetic and control unit 200. The arithmetic and control unit 200 is preliminarily installed with a driver for the printer 300, and is able to print and output various types of information.

(Controller)

The control system of the ophthalmic observation apparatus 1 has a configuration centered on a controller 210 of the arithmetic and control unit 200. The controller 210 includes, for example, the aforementioned microprocessor, RAM, ROM, hard disk drive, and communication interface. The controller 210 is provided with a main controller 211 and storage 213.

(Main Controller)

The main controller 211 performs the aforementioned various kinds of control. Specifically, the main controller 211 controls the LCD 39, a scan driver 70 and a focus driver 80 of the retinal camera unit 2, and further controls the light source unit 101 and a reference driver 130 of the OCT unit 100.

The scan driver 70 is configured, for example, including a servo motor and independently changes the facing direction of the Galvano mirrors 43 and 44. The scan driver 70 consists of one example of the "scanning part" in the invention along with the Galvano mirrors 43 and 44.

The focus driver 80 is configured, for example, including a pulse motor and moves the focusing lens 31 in the optical axis direction. Thereby, the focus position of light towards the fundus Ef is changed.

The reference driver 130 is configured, for example, including a pulse motor and integrally moves the collimator lens 113 as well as the reference mirror 114 along the travelling direction of the reference light LR.

The main controller 211 executes a process of writing data into the storage 213, and a process of reading out the data from the storage 213.

(Operation Mode Controller)

The main controller 211 is provided with an operation mode controller 212. The operation mode controller 212 performs various controls for executing an operation mode. As shown in FIG. 4, the operation mode controller 212 is provided with an operation mode designation part 212a, a fixation direction controller 212b, a scanning pattern controller 212c, an image controller 212d, an analysis controller 212e, an output information controller 212f, and an output controller 212g. The main controller 211 including the operation mode controller 212 is one example of the "control means" of the present invention.

(Operation Mode Designation Part)

When the operator selects one of the multiple operation modes by using the operation part 250, for example, the operation mode designation part 212a designates the selected operation mode as the operation mode to be executed.

Moreover, the operation mode designation part 212a is also capable of automatically or semi-automatically designating the operation mode to be executed at a timing other than when the operator selects an operation mode. This process will be described later as a modified example.

The operation mode designation part 212a sends the designation results of the operation mode to each of the fixation direction controller 212b, the scanning pattern controller 212c, the image controller 212d, the analysis controller 212e, the output information controller 212f, and the output controller 212g.

The operation mode designation part 212a corresponds to one example of the "designating means" of the present invention. Moreover, if the operator manually selects an operation mode, the operation part 250 or other operation device used for that operation and the operation mode designation part 212a correspond to the "designating means".

(Fixation Direction Controller)

The fixation direction controller 212b refers to the operation mode information 214 stored in the storage 213, and identifies the fixation direction associated with the operation mode designated by the operation mode designation part 212a.

Although details will be described later, the operation mode information 214 is information that associates the operational details of each part of the device (the optical system, the image forming part 220, the image processor 230, the display device 3, the display 240, the printer 300, etc.) with each operation mode.

Furthermore, the fixation direction controller 212b controls the fixation optical system and presents the subject eye E with a fixation target for fixating it in the identified fixation direction. As described above, in the present embodiment, the fixation direction is changed by switching the display position of the fixation target in the LCD 39. The fixation direction controller 212b controls the LCD 39 to display the fixation target at the display position corresponding to the identified fixation direction.

(Scanning Pattern Controller)

The scanning pattern controller 212c refers to the operation mode information 214 and identifies the scanning pattern associated with the operation mode designated by the operation mode designation part 212a. As described later, scanning patterns include a three-dimensional scan, a radial scan, a line scan, and a circle scan, etc.

Furthermore, the scanning pattern controller 212c controls the scan drive 70 to scan the signal light LS according to the identified scanning pattern.

(Image Controller)

The image controller 212d refers to the operation mode information 214 and identifies the image type associated with the operation mode designated by the operation mode designation part 212a. Image types include a tomographic image, a three-dimensional image, and a captured image, etc.

It should be noted that if the type of an image to be formed is associated with a scanning pattern, it is possible for the image controller 212d to identify the image type based on the scanning pattern identified by the scanning pattern controller 212c. Examples include cases in which a three-dimensional scan is associated with a three-dimensional image, or cases in which a radial scan (or a line scan or circle scan) is associated with a tomographic image.

Furthermore, the image controller 212d causes the formation of an image of the identified image type. If the identified image type includes a tomographic image, the image controller 212d controls the image forming part 220 to form a tomographic image of the fundus Ef. If the identified image type includes a three-dimensional image, the image controller 212d controls the image forming part 220 and forms multiple tomographic images of the fundus Ef, and also controls the three-dimensional image forming part 231 of the image processor 230 to form a three-dimensional image based on these tomographic images. If the identified image type includes a captured image, the image controller 212d controls the retinal camera unit 2 and acquired a captured image H of the fundus Ef.

(Analysis Controller)

The analysis controller 212e refers to the operation mode information 214 and identifies the analytic process associated with the operation mode designated by the operation mode designation part 212a. As described later, types of analytic processing include a process for analyzing the state of the macula, a process for analyzing the state of the optic papilla, a process for analyzing the presence or severity of glaucoma, and a process for analyzing the presence or severity of macular degeneration, etc.

Furthermore, the analysis controller 212e causes the analytic processor 232 of the image processor 230 to execute the identified analytic process.

(Output Information Controller)

The output information controller 212f refers to the operation mode information 214 and identifies the information type associated with the operation mode designated by the operation mode designation part 212a. This information type is the type of information included in the examination-results information output as the examination results.

The output information controller 212f collects information of the identified information type. The various types of information acquired by the ophthalmic observation apparatus 1 are saved (at least temporarily) in the storage 213. The output information controller 212f selectively reads out information of the identified information type from the storage 213. Alternatively, the output information controller 212f attaches tags or flags to information of the identified information type from among the information stored in the storage 213 to make them identifiable.

Moreover, if it is necessary to generate information of the identified information type, the output information controller 212f collects information required for generating the information, and also controls the image processor 230, etc. to generate the objective information based on the collected information. As one example, if analysis results are being reflected in an image and output, the output information controller 212f reads out the analysis results and the image from the storage 213 and sends them to the image processor 230 to generate an image reflecting the analysis results.

Furthermore, regarding common information items included across all examination-results information, it is not necessary to store them in the operation mode information 214. Common information items include subject information (patient ID, patient name, patient age, etc.), subject-eye information (identification information of the left and right eyes, etc.), examination date and time, physician's name, etc. Moreover, clinical examination results (findings, interview results, etc.) and other examination results (visual acuity values, ocular pressure values, etc.) may also be set as common information items.

(Output Controller)

The output controller 212g refers to the operation mode information 214 and identifies the output layout associated with the operation mode designated by the operation mode designation part 212a. The output layout is information representing the arrangement of each type of information when outputting examination-results information. Output layouts include display layouts for display outputs, or printing layouts for print outputs, etc. Each output layout includes template images of a screen layout for display outputs and a paper layout for print outputs, for example. These template images are preliminarily stored in the storage 213.

The output controller 212g applies the information collected by the output information controller 212f to the identified output layout and outputs the information. To each type of information, identification information such as a tag representing the information type is attached. In the template images, a division pattern that divides the entirety of the screen or paper into presentation regions for each type of information is set. Each presentation region is associated with the identification information of the information. The output controller 212g arranges each of the information collected as examination-results information in the presentation region associated with the identification information.

In the case of a display output, the output controller 212g controls the display device 3 or the display 240, creates display image data based on an image template in which the collected information has been arranged, and displays a screen based on this display image data. In the case of a print output, the output controller 212g creates print image data based on an image template in which the collected information has been arranged, and sends the print image data to the printer 300 for printing.

(Storage)

The storage 213 stores various kinds of data. The data stored in the storage 213 is, for example, image data of OCT images, image data of fundus images, and eye information. The eye information includes information on the eye, for example, information on a subject such as a patient ID and a name, information on identification of left eye or right eye, and so on.

The storage 213 preliminarily stores the operation mode information 214. As described above, the operation mode information 214 is information in which the operational details of each part of the device (the optical system, the image forming part 220, the image processor 230, the display device 3, the display 240, and the printer 300, etc.) are associated with each operation mode. The storage 213 corresponds to the "storage means" of the present invention.

The operation mode information 214 is configured as a table such as that shown in FIG. 5, for example. In the present embodiment, as operation modes that are selectively executed, a "macular examination mode", an "optic-disc examination mode", a "glaucoma examination mode", and a "macular-degeneration examination mode" are set.

Moreover, as operation items, "fixation direction", "scanning pattern", "image type", "analytic process", "information type", "display layout", and "print layout" are set. The operation mode information 214 associates the details of each operation item (operational details) with each operation mode. It should be noted that details of the operational details (particularly for analytic processing) will be described later.

The macular examination mode is an operation mode for examining the state of the macula of the fundus Ef. The macular examination mode is associated with: a "macula fixation direction" as the fixation direction; "three-dimensional (3D)", "radial", and "line" as scanning patterns; "fundus image (captured image)", "tomographic image", and "three-dimensional image" as image types; "retinal thickness analysis" and "normative data comparison" as analytic processes; "fundus image", "representative tomographic image", and "normative comparison diagram" as information types; a "macular template" as the display layout; and a "macular template" as the print layout. Each macular template is for lining up and presenting information of the above information types in a prescribed arrangement. Each macular template corresponds to the "macular examination template" of the present invention.

Furthermore, "normative data comparison" is an analytic process that compares standard values of a healthy eye (in this case, retinal thickness) with the examination results. A diagram showing the comparison results is the "normative comparison diagram".

The optic-disc examination mode is an operation mode for examining the state of the optic papilla of the fundus Ef. The optic-disc examination mode is associated with an "optic-disc fixation direction" as the fixation direction; "circle" and "3D" as scanning patterns; "fundus image", "tomographic image", and "three-dimensional image" as image types; "RNFL thickness analysis", "normative data comparison", and "optic-disc shape analysis" as analytic processes; "fundus image", "representative tomographic image", "normative comparison diagram", and "optic-disc shape parameters" as information types; an "optic-disc template" as the display layout; and an "optic-disc template" as the print layout. Each optic-disc template is for lining up and presenting information of the above information types in a prescribed arrangement. Each optic-disc template corresponds to the "optic-disc examination template" of the present invention. Furthermore, the optic-disc shape parameters are analysis results from the optic-disc shape analysis.

The glaucoma examination mode is an operation mode for examining the presence and severity of glaucoma. The glaucoma examination mode is associated with: a "macula fixation direction" and "optic-disc fixation direction" as fixation directions; "macula 3D" and "optic disc 3D" as scanning patterns; "fundus image", "tomographic image", and "three-dimensional image" as image types; "RNFL thickness analysis", "normative data comparison", and "optic-disc shape analysis" as analytic processes; "fundus image (mosaic image)", "representative tomographic image", "normative comparison diagram (fundus image superimposition)", and "optic-disc shape parameters" as information types; a "glaucoma template" as the display layout; and a "glaucoma template" as the print layout. Each glaucoma template is for lining up and presenting information of the above information types in a prescribed arrangement. Each glaucoma template corresponds to the "glaucoma diagnosis template" of the present invention.

Here, a "mosaic image" is also referred to as a panoramic image, etc., and is a wide-area image obtained by pasting together multiple captured images obtained by separately capturing different parts of the fundus (including the macula and optic papilla). Moreover, "normative data comparison" is an analytic process that compares standard values of a healthy eye (in this case, RNFL thickness) with the examination results. A diagram showing the comparison results is the "normative comparison diagram". "Fundus image superimposition" refers to the superimposition of the normative comparison diagram over a fundus image.

The macular-degeneration examination mode is an operation mode for examining the presence and severity of (age-related) macular degeneration. The macular-degeneration examination mode is associated with: a "macula fixation direction" as the fixation direction; "3D" as the scanning pattern; "fundus image", "tomographic image", and "three-dimensional image" as image types; "retinal thickness analysis" and "Drusen analysis" as analytic processes; "fundus image (Drusen display)", "representative tomographic image", and "Drusen distribution graph/table" as information types; a "macular degeneration template" as the display layout; and a "macular degeneration template" as the print layout. Here, a normative comparison may also be performed as an analytic process. Each macular degeneration template is for lining up and presenting information of the above information types in a prescribed arrangement. Each macular degeneration template corresponds to the "macular degeneration diagnosis template" of the present invention.

Furthermore, drusen refers to waste matter accumulated between Brusch's membrane and the pigment epithelial layer. "Drusen analysis" is an analytic process that obtains the distribution state of drusen. A superimposition of these analysis results with a fundus image is a "drusen display".

The operation mode information according to the present invention is not limited to those shown in FIG. 5. As examples, it is possible to apply operation mode information related to operation modes corresponding to various parts of a subject eye, or to operation modes corresponding to various ophthalmic disorders.

Note that there are differences between medical institutions in the status of their introduction of examination instruments and analytical tools, etc. For example, whereas the latest instruments, etc. are widely prevalent in university hospitals and other advanced medical institutions, many local health clinics do not have the latest instruments, etc. Moreover, each physician has different diagnostic policies, and the images acquired and the analytic processes implemented sometimes differ even for the same diagnosed region or for diagnoses of the same disorder.

Based on considerations of these facts, it is preferable that the operation mode information 214 may be edited in accordance with the medical institution in which the ophthalmic observation apparatus 1 is installed, or with the physician using the ophthalmic observation apparatus 1. These editing operations are performed by, for example, displaying a prescribed editing screen (e.g., a table such as that shown in FIG. 5) on the display 240, and adding or deleting operational details using the operation part 250. Moreover, it is also possible to add and delete operation modes. The operation part 250 used in this manner corresponds to the "operation means" of the present invention.

(Image Forming Part)

An image forming part 220 forms image data of a tomographic image of the fundus Ef based on the detection signals from the CCD image sensor 120. Like the conventional Fourier-Domain OCT, this process includes processes such as noise elimination (noise reduction), filtering, and FFT (Fast Fourier Transform).

The image forming part 220 includes, for example, the aforementioned circuit board and communication interface. It should be noted that "image data" and the "image" presented based on the image data may be identified with each other in this specification.

(Image Processor)

An image processor 230 executes various image processing and analysis on images formed by the image forming part 220. For example, the image processor 230 executes various correction processes such as luminance correction and dispersion correction of images. The image processor 230 is provided with the three-dimensional image forming part 231 and the analytic processor 232.

The image processor 230 includes, for example, the aforementioned microprocessor, RAM, ROM, hard disk drive, circuit board, and so on.

(Three-Dimensional Image Forming Part)

The three-dimensional image forming part 231 executes, for example, an interpolation process of interpolating pixels between tomographic images formed by the image forming part 220, thereby forming image data of a three-dimensional image of the fundus Ef.

Image data of a three-dimensional image refers to image data that the positions of pixels are defined by the three-dimensional coordinates. The image data of a three-dimensional image is, for example, image data composed of three-dimensionally arranged voxels. This image data is referred to as volume data, voxel data, or the like.

For displaying an image based on the volume data, the three-dimensional image forming part 231 executes a rendering process (such as volume rendering and MIP (Maximum Intensity Projection)) on this volume data, and forms image data of a pseudo three-dimensional image taken from a specific view direction. On a display device such as the display 240, this pseudo three-dimensional image is displayed.

Further, it is also possible to form stack data of a plurality of tomographic images as the image data of a three-dimensional image. Stack data is image data obtained by three-dimensionally arranging a plurality of tomographic images obtained along a plurality of scanning lines, based on the positional relation of the scanning lines. That is to say, stack data is image data obtained by expressing a plurality of tomographic images defined by originally individual two-dimensional coordinate systems by a three-dimensional coordinate system (namely, embedding into a three-dimensional space). It should be noted that volume data is formed by performing interpolation process on such stack data.

Moreover, it is possible to form a two-dimensional tomographic image based on a three-dimensional image. This process is executed in the following manner, for example. First, a cross-section is designated within a three-dimensional image. Next, voxels on the designated cross-section are selected. Then, each selected voxel is converted into a two-dimensional pixel to form a two-dimensional tomographic image.

The image forming part 220 and the three-dimensional image forming part 231 is an example of the "image forming means" of the invention.

(Analytic Processor)

The analytic processor 232 performs analytic processes on images of the fundus Ef. Images subject to analysis include tomographic images, three-dimensional images, and captured images, etc. The analytic processor 232 corresponds to the "analysis means" of the present invention.

The analytic processor 232 executes analytic process such as the following, for example: (1) retinal thickness analysis; (2) normative comparison of retinal thickness; (3) RNFL thickness analysis; (4) normative comparison of RNFL thickness; (5) optic-disc shape analysis; and (6) drusen analysis. The retinal thickness analysis and the RNFL thickness analysis are examples of the "layer-thickness analysis" of the present invention. The drusen analysis is an example of the "lesion identification analysis" of the present invention.

It should be noted that the analytic processes executed by the analytic processor 232 are not limited to these. The analytic processor 232 is configured to be able to execute analytic processes corresponding to the examined region of the subject eye or the disorder being examined, etc. Each analytic process is executed based on a dedicated computer program, for example.

The retinal thickness analysis is a process that analyzes a tomographic image or three-dimensional image of the fundus and obtains the thickness distribution of the retina. It should be noted that there are various definitions of retinal thickness. For example, the thickness from the inner limiting membrane to the inner granular layer (internal and external contact of the photoreceptor cells) may be defined as the retinal thickness, or the thickness from the inner limiting membrane to the pigment layer of the retina may be defined as the retinal thickness. The retinal thickness obtained by the retinal thickness analysis can be of one of these definitions.

The retinal thickness analysis is executed in the following manner, for example. First, an OCT image of the fundus is analyzed, and an image region corresponding to prescribed boundary regions (e.g., the inner limiting membrane and the pigment layer of the retina) is identified. Then, the number of pixels between the identified boundary regions is counted to obtain the retinal thickness (i.e. distance in the direction of depth). Note that in addition to the above Patent Document 5, the process of analyzing an OCT image and obtaining the thickness of the fundus layer is also described in Japanese published unexamined application 2007-325831, Japanese published unexamined application 2008-206684, Japanese published unexamined application 2009-61203, and Japanese published unexamined application 2009-66015, etc. by the present applicants.

Furthermore, the boundary region may be designated manually. In this case, an OCT image is displayed on the display 240, this is observed to identify a boundary region, and the identified boundary region is designated using the operation part 250. Moreover, a configuration may also be used in which the boundary region identified through image analysis can be manually modified.

The normative comparison of retinal thickness is an analytic process that compares the retinal thickness obtained through retinal thickness analysis with normative data. The normative data are standard values of the retinal thicknesses (standard thickness) of healthy eyes. The normative data are prepared by measuring the retinal thicknesses of multiple healthy eyes, and obtaining statistical values (mean value, standard deviation etc.) of the measurement results. The normative comparison determines whether or not the retinal thickness of the subject eye E is within the range of the retinal thicknesses of healthy eyes. It should be noted that, in the present invention, the above retinal thickness analysis and normative comparison are collectively referred to as "retinal thickness analysis".

Furthermore, instead of this type of normative comparison, an analytic process may be performed in which the range of the retinal thicknesses of eyes with a disorder is obtained, and a determination is made as to whether the retinal thickness obtained through retinal thickness analysis is within that range.

The RNFL thickness analysis is an analytic process that analyzes a tomographic image or three-dimensional image of a fundus, and obtains the thickness of the RNFL (retinal never fiber layer) of the fundus. As with the retinal thickness analysis, the RNFL analysis is executed by, for example, identifying an image region corresponding to boundary regions of the RNFL, and counting the number of pixels between the identified boundary regions to obtain the RNFL thickness (i.e. distance in the direction of depth).

The normative comparison of the RNFL thickness is an analytic process that compares the RNFL thickness obtained through RNFL thickness analysis with normative data (standard thicknesses). The normative data are also prepared in a similar manner as for the retinal thickness. It should be noted that, in the present invention, the above RNFL thickness analysis and normative comparison are collectively referred to as "RNFL thickness analysis".

The optic-disc shape analysis is an analytic process that analyzes a tomographic image or three-dimensional image of a fundus, and detects openings (cuts, defective regions) in the retina to obtain the shape of the optic papilla. For example, the optic-disc shape analysis analyzes a tomographic image, etc. to identify an image region corresponding to the retina surface of the optic papilla and its surrounding area, and analyzes the identified image region to obtain parameters (optic-disc shape parameters) representing its global shape and local shape (irregularities). Examples of optic-disc shape parameters include the cup diameter, the disc diameter, the rim diameter, and the depth of the optic disc, etc. of the optic papilla.

The drusen analysis is an analytic process that analyzes a captured image (fundus image) or an OCT image, and obtains the state of distribution of drusen in the fundus. This state of distribution includes the position and/or area of the drusen in the fundus.

Drusen analysis based on a captured image is executed by, for example, determining whether the pixel values of each pixel of the captured image are within a prescribed range, and identifying pixels included in the prescribed range. Because drusen is depicted with a characteristic color (pale yellow) in captured images, the range of pixel values corresponding to this characteristic color is preliminarily set as the above prescribed range.

Furthermore, it is also possible to identify an image region corresponding to drusen based on the image brightness (luminance value) or the shape of the drusen (small, roughly circular raised configurations).

Drusen analysis based on an OCT image may be executed by, for example, analyzing an OCT image and identifying an image region corresponding to Bruch's membrane and an image region corresponding to the pigment epithelial layer, and based on the pixel values between these image regions, identifying image regions corresponding to small, roughly circular raised configurations as (candidates of) drusen. This type of identification process of image regions based on shape may be performed through image matching with a template of the relevant shape, for example.

Moreover, as described in Japanese published unexamined application 2008-295804 by the present applicants, it is possible to display an image of the fundus and manually designate image regions corresponding to drusen.

Based on the image regions corresponding to drusen that have been identified in this manner, the analytic processor 232 obtains the distribution of the positions, number and areas, etc. of drusen in the fundus.

Furthermore, it is possible to perform alignment of a captured image and an OCT image. As described in Japanese published unexamined application 2007-252692, for example, this alignment process is executed by forming a two-dimensional image (integrated image) formed by integrating the pixel values of an OCT image (particularly, a three-dimensional image) in the direction of depth, and aligning the integrated image with a captured image.

By performing such alignment, it is possible to associate positions on the captured image with positions on the OCT image. As a result, it is possible to identify positions on the captured image corresponding to the measured positions of retinal thickness or RNFL thickness based on the OCT image. Moreover, it is possible to identify positions on the OCT image (or the captured image) corresponding to the positions of drusen or the optic papilla identified based on the captured image (or the OCT image).

The analytic processor 232 is provided with a macular analyzer 233, an optic disc analyzer 234, a glaucoma analyzer 235, and a macular degeneration analyzer 236. Each analyzer 233-236 is a combination of several of the above multiple analytic processes. In other words, each analyzer 233-236 performs prescribed analytic processes by combining and executing several computer programs corresponding to multiple analytic processes as a macro.

The macula analyzer 233 executes the retinal thickness analysis and the normative comparison of the retinal thickness, and prepares examination results of the state of the macula. The optic disc analyzer 234 executes the RNFL thickness analysis, the normative comparison of the RNFL thickness, and the optic-disc shape analysis, and prepares examination results of the state of the optic disc. The glaucoma analyzer 235 executes the RNFL thickness analysis, the normative comparison of the RNFL thickness, and the optic-disc shape analysis, and prepares examination results of glaucoma. The macular degeneration analyzer 236 executes the retinal thickness analysis and the drusen analysis, and prepares examination results of macular degeneration. Furthermore, the macular degeneration analyzer 236 may execute the normative comparison of the retinal thickness.

These analyzers 233-236 are provided to correspond to the operational details of the analytic processes in the operation mode information 214. Furthermore, instead of executing the analytic processes as a preset macro as described above, it is possible to select the computer programs of analytic processes subject to execution based on the operation mode information 214, and execute the analytic processes based on the selected computer programs.

(Display and Operation Part)

The display 240 is configured including a display device of the aforementioned arithmetic and control unit 200. Furthermore, the display 240 may also include various display devices such as a touch panel monitor, etc. provided with the case of the retinal camera unit 2.

The operation part 250 is configured including an operation device of the aforementioned arithmetic and control unit 200. Furthermore, the operation part 250 may also include various kinds of buttons or keys provided with the case of the ophthalmic observation apparatus 1 or its outside. For example, if the retinal camera unit 2 has a case that is the same as conventional fundus cameras, a joy stick, operation panel, etc. provided with the case may also be included in the operation part 250.

The display 240 and the operation part 250 do not need to be composed as separate devices. For example, like a touch panel LCD, a device in which the display function and the operation function are integrated can be used.

[Scan with Signal Light and OCT Image]

A scan with the signal light LS and an OCT image will be described.

The scanning patterns of the signal light LS by the ophthalmic observation apparatus 1 is, for example, a horizontal scan, vertical scan, cruciform scan, radial scan, circular scan, concentric scan, and helical scan. These scanning patterns are selectively used as necessary in consideration of an observation site of the fundus, an analysis target (the retinal thickness or the like), a time required to scan, the accuracy of a scan, and so on.

A horizontal scan is a scan with the signal light LS in the horizontal direction (x-direction). The horizontal scan includes an aspect of scanning with the signal light LS along a plurality of scanning lines extending in the horizontal direction arranged in the vertical direction (y-direction). In this aspect, it is possible to set any interval between scanning lines. By setting the interval between adjacent scanning lines to be sufficiently narrow, it is possible to form the aforementioned three-dimensional image (three-dimensional scan). A vertical scan is also performed in a similar manner. Linear scanning patterns such as the horizontal scan and the vertical scan are integrally called a line scan.

A cruciform scan is a scan with the signal light LS along a cross-shape trajectory formed by two linear trajectories (line trajectories) orthogonal to each other. A radial scan is a scan with the signal light LS along a radial trajectory formed by a plurality of line trajectories arranged at predetermined angles. The cruciform scan is an example of the radial scan.

A circular scan is a scan with the signal light LS along a circular trajectory. A concentric scan is a scan with the signal light LS along a plurality of circular trajectories arranged concentrically around a predetermined center position. The circular scan is regarded as a special example of the concentric scan. A helical scan is a scan with the signal light LS along a helical trajectory while making the turning radius gradually smaller (or greater).

Because the galvano mirrors 43, 44 are configured to scan the signal light LS in mutually perpendicular directions, it is possible to independently scan the signal light LS in the x-direction and the y-direction. Furthermore, by simultaneously controlling the orientations of the galvano mirrors 43, 44, it is possible to scan the signal light LS along any trajectory on the xy plane. As a result, various scanning patterns such as those described above may be realized.

By scanning the signal light LS in the mode described above, it is possible to form tomographic images of the depth-wise direction (z-direction) along scanning lines (scan trajectory). Moreover, in a case that the interval between scanning lines is narrow, it is possible to form the aforementioned three-dimensional image.

A region on the fundus Ef subjected to scanning by the signal light LS as above is referred to as a scanning region. A scanning region in three-dimensional scanning is a rectangular-shaped region in which a plurality of horizontal scans are arranged. Furthermore, a scanning region in a concentric circular scan is a disc-shaped region surrounded by the trajectories of a circular scan of a maximum diameter. Moreover, the scanning region in a radial scan is a disc-shaped (or polygonal-shaped) region linking end positions of scanning lines.

[Operations]

Figure 6:
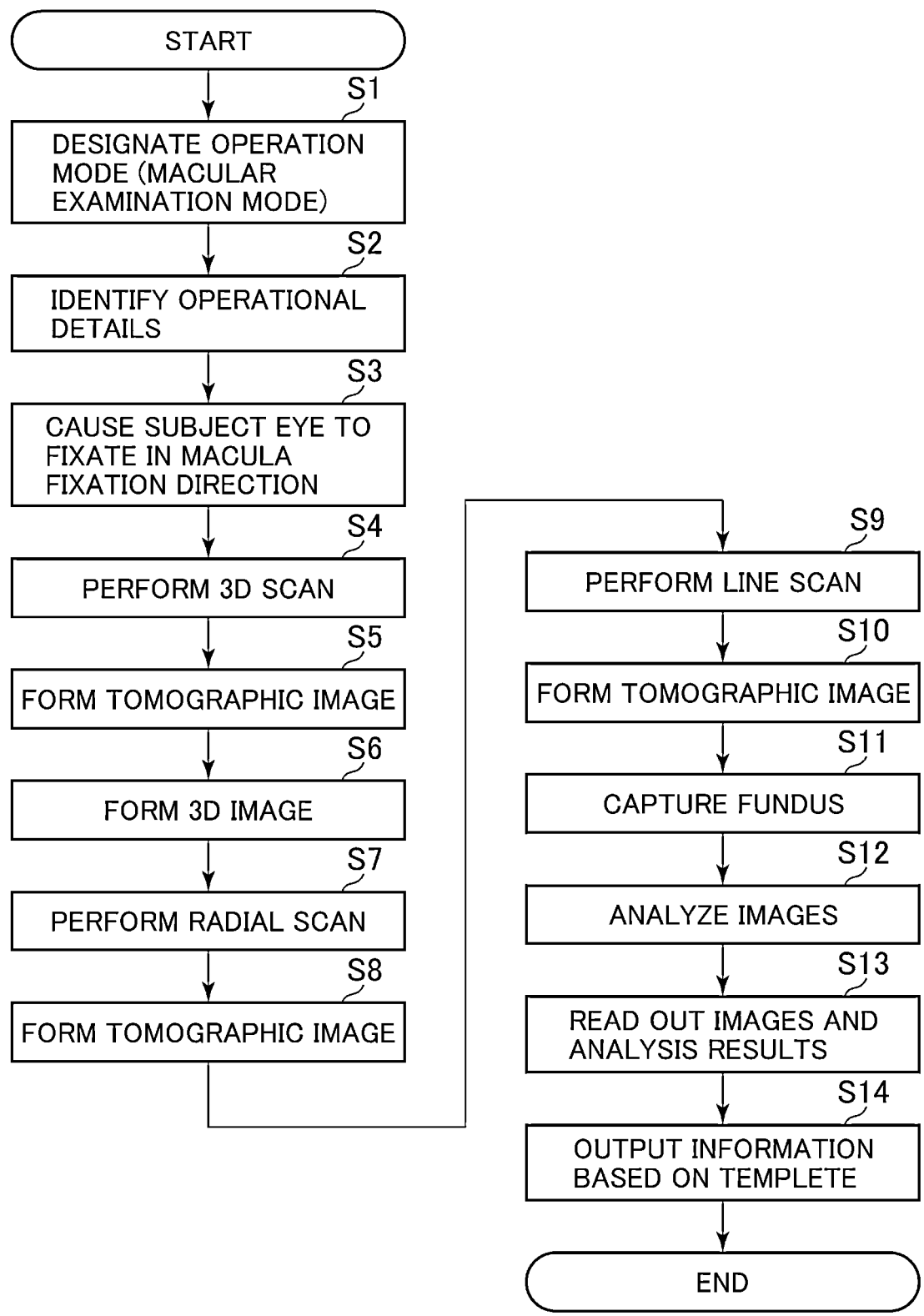
FIG. 6 is a flowchart showing an example of an action of an embodiment of an ophthalmic observation apparatus according to the present invention.

Operations of the ophthalmic observation apparatus 1 will be described. An operational example of the ophthalmic observation apparatus 1 is shown in FIG. 6. Alignment and focusing of the subject eye E is presumed to have been performed already. Alignment may be performed manually by the operator, or may be performed automatically based on an image of the anterior segment of the eye.

First, the main controller 211 displays a prescribed screen for selecting an operation mode on the display 240. The operator selects an operation mode using the operation part 250. The operation mode designation part 212a designates the selected operation mode, and sends the designation results to each controller 212b-212g (S1). In this operational example, a case in which the macular examination mode has been designated will be described.

Each controller 212b-212g refers to the operation mode information 214 to identify the operational details (S2). Specifically, the fixation direction controller 212b identifies the "macula fixation direction" as the fixation direction of the subject eye, the scanning pattern controller 212c identifies "3D", "radial", and "line" as the scanning patterns of the signal light LS, the image controller 212d identifies "fundus image", "tomographic image", and "3D image" as the image types, the analysis controller 212e identifies "retinal thickness analysis" and "normative comparison" as the analytic processes, the output information controller 212f identifies "fundus image", "representative tomographic image", and "normative comparison diagram" as the information types, and the output controller 212g identifies the "macular template" as the display layout while also identifying the "macular template" as the print layout.

The fixation direction controller 212b controls the LCD 39, displays a fixation target at a position on the screen corresponding to the macula fixation direction, and thereby causes the subject eye E to fixate in the macula fixation direction (S3).

In this fixated state, the main controller 211 controls the light source unit 101 to output a low-coherence light L0, while the scanning pattern controller 212c controls the scan drive 70 to scan the signal light LS based on this low-coherence light L0 along a scanning pattern for a three-dimensional scan (S4). In the three-dimensional scan, the signal light LS is sequentially irradiated on multiple irradiation positions arranged in the form of lattice points. The OCT unit 100 causes the signal light LS and the reference light LR to overlap to generate and detect the interference light LC. The detected signals are transmitted to the arithmetic and control unit 200. Note that it is also possible to start the above OCT measurement in response to a prescribed operation (pressing of an operation button, etc.) by the operator, or to start it automatically by determining the fixated state based on an image of the fundus Ef (observation image K, etc.).

The image controller 212d controls the image forming part 220 to form tomographic images based on the detected signals from the OCT unit 100 (S5). Because a three-dimensional scan has been executed, multiple tomographic images along multiple parallel scanning lines are generated. The main controller 211 stores the multiple formed tomographic images in the storage 213.

Furthermore, the image controller 212d sends these tomographic images to the image processor 230, and also controls the three-dimensional image forming part 231 to form a three-dimensional image (S6). The main controller 211 stores the formed three-dimensional image in the storage 213. This three-dimensional image depicts the configuration of the macula of the fundus Ef and the surrounding area.

Next, the main controller 211 and the scanning pattern controller 212c cause the execution of a radial scan in a manner similar to step 4 (S7). In the radial scan, the signal light LS is sequentially irradiated on multiple irradiation positions arranged radially. The image controller 212d controls the image forming part 220 to form tomographic images based on detected signals obtained from the radial scan (S8). As a result, multiple tomographic images arranged radially with the position of the macula in approximately the center are obtained. The main controller 211 stores the obtained multiple tomographic images in the storage 213.

Furthermore, the main controller 211 and the scanning pattern controller 212c cause the execution of a line scan in a manner similar to step 4 (S9). In a line scan, the signal light LS is sequentially irradiated on multiple irradiation positions arranged linearly. The image controller 212d controls the image forming part 220 to form tomographic images based on detected signals obtained from the line scan (S10). As a result, tomographic images along a scanning line passing through the macula are obtained. The main controller 211 stores the obtained tomographic images in the storage 213. With the above, the OCT measurement is ended.

Next, the image controller 212d controls the retinal camera unit 2 to capture the fundus Ef (S11). The main controller 211 stores the captured image in the storage 213.

The analysis controller 212e sends the acquired tomographic images, three-dimensional images, and captured images (fundus images) to the image processor 230, and controls the macula analyzer 233 to execute the retinal thickness analysis and a normative comparison (S12). The macula analyzer 233 generates a normative comparison diagram as the analysis results. The main controller 211 stores the generated normative comparison diagram in the storage 213.

In response to an output request for examination results made using the operation part 250, for example, the output information controller 212f reads out the fundus image (captured image), the representative tomographic image (e.g., a tomographic image obtained through the line scan), and the normative comparison diagram from the storage 213 (S13). At this time, information related to the abovementioned common information items is also read out.

The output controller 212g reads out the macular template for display or printing from the storage 213. Furthermore, the output controller 212g applies the information read out in step 13 to the macular template to create image data for output (image data for display and/or image data for printing), and controls the display 240 or the printer 300 based on the image data for output to output a display screen or a printed image (S14). With the above, operations related to the macular examination mode are ended.

If another operation mode is designated, as with the above macular examination mode, the processing is executed based on the operation mode information 214. Cases in which another operation mode is designated are briefly described below.

If the optic-disc examination mode is designated, a circle scan and a three-dimensional scan are sequentially executed while the subject eye E is fixated in the optic-disc fixation direction. Based on detected signals based on the circle scan, the arithmetic and control unit 200 forms a tomographic image along a circular scanning line with (the center of the optic disc of) the optic papilla at approximately the center. Moreover, the arithmetic and control unit 200 forms multiple tomographic images based on detected signals based on the three-dimensional scan, and forms a three-dimensional image based on these tomographic images. This three-dimensional image is an image depicting the optic papilla and the surrounding area. Moreover, the retinal camera unit 2 captures the fundus Ef. The optic disc analyzer 234 executes the RNFL thickness analysis, the normative comparison, and the optic-disc shape analysis based on the acquired OCT image, etc., and creates a normative comparison diagram as the analysis results. The arithmetic and control unit 200 distributes the fundus image, the representative tomographic image (e.g., a tomographic image based on a circle scan), the normative comparison diagram and the optic-disc shape parameters to the optic-disc template and outputs them.

If the glaucoma examination mode is designated, a three-dimensional scan is executed while keeping the subject eye E fixated in the macula fixation direction, and a three-dimensional image depicting the macula and the surrounding area is formed. Next, the fixation direction of the subject eye E is changed to the optic-disc fixation direction to execute a three-dimensional scan, and a three-dimensional image depicting the optic papilla and the surrounding area is formed. Moreover, the retinal camera unit 2 captures the fundus Ef. The glaucoma analyzer 235 executes an RNFL thickness analysis, a normative comparison, and an optic-disc shape analysis based on an acquired OCT image, etc., and creates a normative comparison diagram as the analysis results. The arithmetic and control unit 200 distributes the fundus image, the representative tomographic image, the normative comparison diagram, and the optic-disc shape parameters to the glaucoma template and outputs them. This representative tomographic image is, for example, a tomographic image that is formed based on a three-dimensional image of the macula and has the position of the macula as the cross-section, and a tomographic image that is formed based on a three-dimensional image of the optic papilla and has the position of the optic papilla as the cross-section.

If the macular degeneration examination mode is designated, a three-dimensional scan is executed while keeping the subject eye E fixated in the macula fixation direction, and a three-dimensional image depicting the macula and the surrounding area is formed. Moreover, the retinal camera unit 2 captures the fundus Ef. The macular degeneration analyzer 236 executes the retinal thickness analysis based on an acquired OCT image, and also executes the drusen analysis based on the OCT image or a captured image (fundus image). The arithmetic and control unit 200 distributes the fundus image, the representative tomographic image, the results of the retinal thickness analysis, and the results of the drusen analysis to the macular degeneration template and outputs them. This representative tomographic image is, for example, a tomographic image that is formed based on a three-dimensional image of the macula and has the position of the macula as the cross-section.

[Actions and Effects]

The actions and effects of the ophthalmic observation apparatus 1 as described above will be described.

The ophthalmic observation apparatus 1 includes an optical system that divides the low-coherence light L0 into the signal light LS and the reference light LR and causes the signal light LS that has passed through the subject eye E (fundus Ef) to overlap with the reference light LR that has passed through a reference light path to generate and detect the interference light LC, and forms an OCT image of the subject eye E (fundus Ef) based on the detection results of the interference light LC. Furthermore, the ophthalmic observation apparatus 1 performs analytic processing for the formed OCT image, and outputs examination-results information including the analysis results.

Moreover, the ophthalmic observation apparatus 1 is capable of selectively executing multiple operation modes. The ophthalmic observation apparatus 1 preliminarily stores the operation mode information 214 that associates various operational details with each operation mode. When one operation mode is designated, the ophthalmic observation apparatus 1 refers to the operation mode information 214 to identify the operational details associated with the operation mode, and controls the optical system, the image forming part 220, the three-dimensional image forming part 231, the analytic processor 232, the display 240, and the printer 300, etc. based on the identified operational details.

Note that the mode of output of the examination-results information includes display output and print output. The display 240, the display device 3, and the printer 300 are examples of the "output means" of the present invention. Furthermore, if the examination-results information is transmitted to an external device, a communication interface such as a LAN card, etc. functions as the output means. Moreover, if the examination-results information is stored in storage medium, the drive device that stores the information in the storage medium functions as the output means.

Furthermore, the ophthalmic observation apparatus 1 includes an image-capturing means (retinal camera unit 2) that captures the fundus Ef. If the operational details of the image-capturing means are associated with the designated operation mode (i.e., if the acquisition of a color image or a fluorescent image, etc. is stored in the operation mode information 214), the ophthalmic observation apparatus 1 controls the image-capturing means based on the operational details to form a captured image H of the fundus Ef. The formed captured image H is output as the examination-results information together with the OCT image and the analysis results.

According to this type of ophthalmic observation apparatus 1, it is possible to automatically execute a series of processes according to a designated operation mode, and it is therefore possible to acquire information used for the diagnosis of the subject eye E easily and without excess or deficiency.

MODIFIED EXAMPLES

The configuration described above is merely one example for favorably implementing the present invention. Therefore, it is possible for a person who intends to implement the present invention to properly make arbitrary modification within the scope of the present invention. In the following explanation, the same symbols are used for the similar part to the above embodiment.

Modified Example 1

As in follow-up observations and pre- and post-operative observations, etc., the same examination may be repeated. In such a case, it is useful if the same operation mode as that used in a past examination is automatically designated. In the present variation, a configuration is described in which it is possible to automatically designate the same operation mode as that used in a past examination.

The ophthalmic observation apparatus according to the present variation includes an input means that inputs patient identification information such as patient ID and patient name, etc. If the patient identification information is input manually, the input means is configured by the operation part 250, for example. Moreover, if the patient identification information is recorded in a patient card, etc. to which a storage medium is attached, the patient identification information may be read out and input from this storage medium. The input means in this case includes a reader device for the storage medium.

Moreover, if the patient identification information is input automatically, the input means is configured by the main controller 211, for example. Examples of cases of automatic input include cases in which an electronic medical chart of the patient is already open and the patient identification information stored in the electronic medical chart is automatically input.

When an examination is performed using an operation mode, the main controller 211 associates (the identification information of) the operation mode with the patient identification information input by the input means, and stores them in the storage 213. At this time, it is preferable to also store information on the date and time of the examination, etc. The main controller 211 executes this process every time the examination is performed.

When patient identification information is input at the time of starting an examination, etc., the operation mode designation part 212a retrieves the operation mode stored together with the patient identification information in the past from the storage 213. If retrieval is not successful, the operation mode controller 212 displays a screen for selecting an operation mode on the display 240, and shifts to a manual designation of the operation mode.

If the past operation mode is retrieved, the operation mode controller 212 refers to the operation mode information 214 and identifies the operation details associated with the retrieved operation mode. Furthermore, based on the identified operational details, the operation mode controller 212 controls the optical system, the image forming part 220, the image processor 230, the display 240, etc. to execute the processing of this operation mode.

Modified Example 2

In cases of repeating the same examination, as is the case for follow-up observations, etc., multiple examinations may be performed. The implementation interval of each examination is not necessarily the same. For example, examination A may be performed at an interval of two weeks, and examination B may be performed at an interval of three weeks. In such a case, it is useful if it is possible to automatically identify the examination to be performed today and automatically designate an operation mode. In the present variation, a configuration in which it is possible to realize such a process is described.

The ophthalmic observation apparatus according to the present variation includes an input means similar to that of Modified example 1. Furthermore, the ophthalmic observation apparatus is provided with a timekeeping means that keeps the current date and time. This timekeeping means is configured by, for example, a microprocessor that includes a timekeeping function.

As in the above embodiment, in the operation mode information of the present variation, operational details are associated with each operation mode, and information representing the time intervals for performing examinations in that operation mode (examination intervals) is also associated.

The operation mode controller 212 stores the operation mode for each examination in the storage 213 together with the input patient identification information and the date and time kept by the timekeeping means (date and time of examination). As a result, the patient identification information and the date and time of the examination are associated with each examination (each operation mode) that is performed.

When patient identification information is input at the time of starting an examination, etc., the operation mode designation part 212a retrieves the operation mode and the date and time of examination stored together with the patient identification information in the past from the storage 213. If retrieval is not successful, the operation mode controller 212 displays a screen for selecting an operation mode on the display 240, and shifts to manual designation of an operation mode.

If retrieval is successful, the operation mode designation part 212a calculates the difference between the retrieved date and time of the past examination and the current date and time being kept by the timekeeping means, and obtains the examination interval. Furthermore, the operation mode designation part 212a refers to the operation mode information and selects the operation mode associated with the obtained examination interval. At this time, it is not necessary for the obtained examination interval and the examination interval stored in the operation mode information to be equal. The operation mode designation part 212a may identify the examination interval closest to the obtained examination interval from the operation mode information, and select the operation mode associated with the identified examination interval. As a result, even if there is some margin of error with the actual examination interval, the operation mode for the current examination may be selected.

The operation mode controller 212 refers to the operation mode information and identifies the operational details associated with the selected operation mode. Furthermore, based on the identified operational details, the operation mode controller 212 controls the optical system, the image forming part 220, the image processor 230, and the display 240, etc. to execute the processing of the operation mode.

Modified Example 3

There are cases in which the examination to be performed next time is different depending on the examination results. For example, examination A may be performed this time if there were no abnormalities in the examination performed previously, and examination B may be performed this time if an abnormality was observed in the previous examination. In such a case, it is useful if the operational details can be automatically changed depending on the results of the previous examination. In the present variation, a configuration in which it is possible to realize such a process is described.

The ophthalmic observation apparatus according to the present variation includes an input means similar to that of Modified example 1. If there is an abnormality in the analysis results obtained by the analytic processor 232, the operation mode controller 212 stores information indicating as such (abnormal-presence information) in the storage 213 together with patient identification information input by the input means. Note that the presence or absence of an abnormality may be determined, for example, based on whether the thickness of a layer is within an acceptable range (standard thickness) in a normative comparison.

As in the above embodiment, in the operation mode information of the present variation, operational details are associated with each operation mode, and operational-change information representing changes to operational details in cases in which an abnormality is present is also associated. The operational-change information is for changing the operational details to, for example, perform analytic process B in addition to analytic process A if an abnormality is present. Moreover, the operational-change information may be for switching to an examination of a different operation mode, or adding an examination of a different operation mode if an abnormality is present.

When patient identification information is input at the time of starting an examination, etc., the operation mode designation part 212a retrieves the abnormal-presence information stored together with the patient identification information in the past from the storage 213. If no abnormal-presence information is retrieved, the original operation mode is executed without changing the operational details.

If abnormal-presence information is retrieved, the operation mode designation part 212a changes the operational details of the operation mode based on the operational-change information. Based on the changed operational details, the operation mode controller 212 controls the optical system, the image forming part 220, the image processor 230, and the display 240, etc. to execute the processing of this operation mode.

Modified Example 4

In the above embodiment, normative data comparison in which the retinal thickness or RNFL thickness is compared with standard values (one example of a prescribed standard thickness) of healthy eyes has been described. In the present variation, another example of the prescribed standard thickness is described. Furthermore, the prescribed standard thickness is not limited to the above embodiment or the following variation.

The first example is values of the eye on the opposite side from the subject eye E (referred to as the "opposite eye"). The present variation may be applied to cases in which the retinal thickness and/or RNFL thickness (referred to as "retinal thickness, etc.") of the opposite eye have been measured. The present variation is effective for cases in which, for example, the opposite eye is a healthy eye or has a milder disorder than the subject eye E. Moreover, by comparing the retinal thickness, etc. of the subject eye E with the retinal thickness, etc. of the opposite eye in this manner, it is possible to determine the difference in the retinal thickness, etc. between the right and left eyes.

The second example is measured values from a past examination. In the present variation, the retinal thickness, etc. obtained in the present examination is compared with the retinal thickness, etc. obtained in a past (e.g., previous) examination. As a result, it is possible to determine changes in the retinal thickness, etc. from the past. Moreover, by repeating this type of comparison, it is possible to determine changes over time in the retinal thickness, etc.

Other Modified Examples

In the operation mode information 214 of the above embodiment, the fixation direction, the scanning pattern, the image type, the analytic process, the information type, the display layout, and the print layout are set as operation items, but it is possible to create and use operation mode information in which several of these are set as operation items. Note that, to make processing automatic, it is preferable to set many operation items.

In the above embodiment, the position of the reference mirror 114 is changed so as to change an optical path length difference between the optical path of the signal light LS and the optical path of the reference light LR. However, a method for changing the optical path length difference is not limited thereto. For example, it is possible to change the optical path length difference by moving the retinal camera unit 2 and the OCT unit 100 with respect to the eye E to change the optical path length of the signal light LS. Moreover, in a case that an object is not a living site or the like, it is also effective to change the optical path length difference by moving the object in the depth direction (z-direction).

The computer program used in the above embodiments can be stored in any kind of recording medium that can be read by a computer. As this recording medium, for example, an optical disk, a magneto-optic disk (CD-ROM, DVD-RAM, DVD-ROM, MO, and so on), and a magnetic storage (a hard disk, a Floppy Disk™, ZIP, and so on) can be used. Moreover, it is possible to store into a storing device such as a hard disk drive and a memory.

Besides, it is possible to transmit/receive this program through a network such as internet or LAN etc.

EXPLANATION OF THE SYMBOLS

1 Ophthalmic observation apparatus
2 Retinal camera unit
3 Display device
10 Illumination optical system
11 Observation light source
15 Imaging light source
30 Imaging optical system
31 Focusing lens
35, 38 CCD image sensor
39 LCD
43, 44 Galvano mirror
50 Alignment optical system
60 Focus optical system
70 Scan drive
80 Focus drive
100 OCT unit
101 Light source unit
114 Reference mirror
118 Diffraction grating
120 CCD image sensor
130 Reference driver
200 Arithmetic and control unit
210 Controller
211 Main controller
212 Operation mode controller
212a Operation mode designation part
212b Fixation direction controller
212c Scanning pattern controller
212d Image controller
212e Analysis controller
212f Output information controller
212g Output controller
213 Storage
214 Operation mode information
220 Image forming part
230 Image processor 231 3-dimensional image forming part
232 Analytic processor
233 Macula analyzer
234 Optic disc analyzer
235 Glaucoma analyzer
236 Macular degeneration analyzer
240 Display
250 Operation part
300 Printer
E Subject eye
Ef Fundus
K Observation image
H Captured image
G Tomographic image

What is claimed is:

1. An ophthalmic observation apparatus comprising:
an optical system that divides light output from a light source unit into a signal light and a reference light, overlaps said signal light that has passed through a subject eye and the reference light that has passed through a reference light path, and generates and detects interference light;
an image forming means that, based on the detection results of said interference light by said optical system, forms an image of said subject eye;
an analysis means that analyzes said formed image;
an output means that outputs examination-results information including the image analysis results by said analysis means;
a storage means that preliminarily stores operation mode information in which each of a plurality of operation modes corresponding to examination types is associated with the operational details of at least one of said optical system, said image forming means, said analysis means, and said output means;
a designating means that designates one of said plurality of operation modes; and
a control means that refers to the operation mode information stored in said storage to identify the operational details associated with said designated operation mode, and controls said optical system, said image forming means, said analysis means, and/or said output means based on said identified operational details, wherein
said optical system includes a fixation optical system that present said subject eye with a fixation target for fixating said subject eye in a prescribed fixation direction,
in said operation mode information, fixation directions by said fixation optical system are associated with each of said plurality of operation modes, and
said control means refers to said operation mode information to identify the fixation direction associated with said designated operation mode, and also controls said fixation optical system to present said fixation target for fixating in the identified fixation direction.

2. The ophthalmic observation apparatus according to claim 1, wherein
said fixation optical system includes a display device that displays said fixation target, and a projection optical system that projects said displayed fixation target to said subject eye,
in said operation mode information, display positions of said fixation target on said display device are associated as the fixation directions for each of said plurality of operation modes, and
said control means refers to said operation mode information to identify the display position associated with said designated operation mode, and also controls said display device to display said fixation target at the identified display position on said display device.

3. An ophthalmic observation apparatus comprising:
an optical system that divides light output from a light source unit into a signal light and a reference light, overlaps said signal light that has passed through a subject eye and the reference light that has passed through a reference light path, and generates and detects interference light;
an image forming means that, based on the detection results of said interference light by said optical system, forms an image of said subject eye;
an analysis means that analyzes said formed image;
an output means that outputs examination-results information including the image analysis results by said analysis means;
a storage means that preliminarily stores operation mode information in which each of a plurality of operation modes corresponding to examination types is associated with the operational details of at least one of said optical system, said image forming means, said analysis means, and said output means;
a designating means that designates one of said plurality of operation modes; and
a control means that refers to the operation mode information stored in said storage to identify the operational details associated with said designated operation mode, and controls said optical system, said image forming means, said analysis means, and/or said output means based on said identified operational details, wherein
said optical system includes a scanning means that scans the irradiation position of said signal light on said subject eye,
in said operation mode information, each of said plurality of operation modes is associated with a scanning pattern of said irradiation position by said scanning means, and with an image type formed by said image forming means, and
said control means refers to said operation mode information to identify the scanning pattern and image type associated with said designated operation mode, and also controls said scanning means to scan the irradiation position of said signal light in the identified scanning pattern, and controls said image forming means to form an image of said subject eye of the identified image type.

4. An ophthalmic observation apparatus comprising:
an optical system that divides light output from a light source unit into a signal light and a reference light, overlaps said signal light that has passed through a subject eye and the reference light that has passed through a reference light path, and generates and detects interference light;
an image forming means that, based on the detection results of said interference light by said optical system, forms an image of said subject eye;
an analysis means that analyzes said formed image;
an output means that outputs examination-results information including the image analysis results by said analysis means;
a storage means that preliminarily stores operation mode information in which each of a plurality of operation modes corresponding to examination types is associated with the operational details of at least one of said optical system, said image forming means, said analysis means, and said output means;
a designating means that designates one of said plurality of operation modes; and a control means that refers to the operation mode information stored in said storage to identify the operational details associated with said designated operation mode, and controls said optical system, said image forming means, said analysis means, and/or said output means based on said identified operational details, wherein said analysis means is capable of executing a plurality of sets of analytic processing, including layer-thickness analysis that obtains the thickness of a prescribed layer of said subject eye, and lesion identification analysis that identifies the position of a lesion in said subject eye, in said operation mode information, each of said plurality of operation modes is associated with at least one of said plurality of sets of analytic processing, and said control means refers to said operation mode information to identify the analytic processing associated with said designated operation mode, and also controls said analysis means to execute the identified analytic processing.

5. An ophthalmic observation apparatus comprising:

an optical system that divides light output from a light source unit into a signal light and a reference light, overlaps said signal light that has passed through a subject eye and the reference light that has passed through a reference light path, and generates and detects interference light;

an image forming means that, based on the detection results of said interference light by said optical system, forms an image of said subject eye;

an analysis means that analyzes said formed image;

an output means that outputs examination-results information including the image analysis results by said analysis means;

a storage means that preliminarily stores operation mode information in which each of a plurality of operation modes corresponding to examination types is associated with the operational details of at least one of said optical system, said image forming means, said analysis means, and said output means;

a designating means that designates one of said plurality of operation modes; and a control means that refers to the operation mode information stored in said storage to identify the operational details associated with said designated operation mode, and controls said optical system, said image forming means, said analysis means, and/or said output means based on said identified operational details, wherein in said operation mode information, each of said plurality of operation modes is associated with an information type included in said examination-results information, and with an output layout of said examination-results information by said output means, and said control means refers to said operation mode information to identify the information type and output layout associated with said designated operation mode, and also controls said output means to arrange and output said examination-results information including the identified information type in the identified output layout.

6. An ophthalmic observation apparatus comprising:

an optical system including: a fixation optical system that presents a subject eye with a fixation target for fixating said subject eye in a prescribed fixation direction; a dividing means that divides light output from a light source unit into a signal light and a reference light; a scanning means that scans the irradiation position of said signal light on said subject eye; an overlapping means that overlaps said signal light that has passed through said subject eye and the reference light that has passed through a reference light path to generate interference light; and a detection means that detects said generated interference light;

an image forming means that forms an image of said subject eye based on the detection results of said interference light by said detection means;

an analysis means that is capable of executing a plurality of sets of analytic processing, including layer-thickness analysis that analyzes said formed image to obtain the thickness of a prescribed layer of said subject eye, and lesion identification analysis that analyzes said formed image to identify the position of a lesion in said subject eye;

an output means that outputs examination-results information including the image analysis results from said analysis means;

a storage means that preliminarily stores operation mode information in which each of a plurality of operation modes corresponding to examination types is associated with a fixation direction by said fixation optical system, a scanning pattern of said irradiation position by said scanning means, an image type formed by said image forming means, at least one of said plurality of sets of analytic processing, an information type included in said examination-results information, and an output layout of said examination-results information from said output means;

a designating means that designates one of said plurality of operation modes; and a control means refers to said operation mode information to identify the fixation direction, scanning pattern, image type, analytic processing, information type, and output layout associated with said designated operation mode, and also controls said fixation optical system to present said fixation target for fixating in the identified fixation direction, controls said scanning means to scan the irradiation position of said signal light in the identified scanning pattern, controls said image forming means to form an image of said subject eye of the identified image type, controls said analysis means to execute the identified analytic processing, and controls said output means to arrange and output said examination-results information including the identified information type in the identified output layout.

7. The ophthalmic observation apparatus according to claim 6, wherein said plurality of operation modes includes a macular examination mode for examining the macula of the fundus, and in said operation mode information, in relation to said macular examination mode: a macula fixation direction for irradiating the macula and the surrounding area with said signal light is associated as said fixation direction; a three-dimensional scan that sequentially irradiates said signal light on a plurality of irradiation positions arranged in the form of lattice points, a radial scan that sequentially irradiates said signal light on a plurality of irradiation positions arranged radially, or a line scan that sequentially irradiates said signal light on a plurality of irradiation positions arranged linearly is associated as said scanning pattern; as said image type, a three-dimensional image is associated if said scanning pattern is said three-dimensional scan, or a tomographic image is associated if said scanning pattern is said radial scan or said line scan; a retinal thickness analysis that obtains the retinal thickness and compares it with a prescribed standard thickness is associated as said analytic processing; a tomographic image and the results of said comparison by said retinal thickness analysis are associated as said information type; and a macular examination template that arranges said tomographic image and the results of said comparison in a prescribed arrangement is associated as said output layout.

8. The ophthalmic observation apparatus according to claim 6, wherein said plurality of operation modes includes an optic-disc examination mode for examining the optic papilla of the fundus, and in said operation mode information, in relation to said optic-disc examination mode: an optic-disc fixation direction for irradiating the optic papilla and the surrounding area with said signal light is associated as said fixation direction; a circle scan that sequentially irradiates said signal light on a plurality of irradiation positions arranged circularly, or a three-dimensional scan that sequentially irradiates said signal light on a plurality of irradiation positions arranged in the form of lattice points is associated as said scanning pattern; as said image type, a tomographic image is associated if said scanning pattern is said circle scan, or a three-dimensional image is associated if said scanning pattern is said three-dimensional scan; an RNFL (retinal nerve fiber layer) thickness analysis that obtains the RNFL thickness and compares it with a prescribed standard thickness, and an optic-disc shape analysis that detects the opening of the retina and analyzes the shape of the optic papilla are associated as said analytic processing; a tomographic image, the results of said comparison from said RNFL thickness analysis, and the results of said optic-disc shape analysis are associated as said information type; and an optic-disc examination template that arranges said tomographic image, the results of said comparison, and the results of said optic-disc shape analysis in a prescribed arrangement is associated as said output layout.

9. The ophthalmic observation apparatus according to claim 6, wherein said plurality of operation modes includes a glaucoma examination mode for performing glaucoma examinations, and in said operation mode information, in relation to said glaucoma examination mode: a macular fixation direction for irradiating the macula and the surrounding area with said signal light, and an optic-disc fixation direction for irradiating the optic papilla and the surrounding area with said signal light are associated as said fixation direction; a three-dimensional scan that sequentially irradiates said signal light on a plurality of irradiation positions arranged in the form of lattice points is associated as said scanning pattern; a three-dimensional image of the macula and the surrounding area and a three-dimensional image of the optic papilla and the surrounding area are associated as said image type; an RNFL (retinal nerve fiber layer) thickness analysis that obtains the RNFL thickness and compares it with a prescribed standard thickness, and an optic-disc shape analysis that detects the opening of the retina and analyzes the shape of the optic papilla are associated as said analytic processing; a tomographic image, the results of said comparison from said RNFL thickness analysis, and the results of said optic-disc shape analysis are associated as said information type; and a glaucoma diagnosis template that arranges said tomographic image, the results of said comparison, and the results of said optic-disc shape analysis in a prescribed arrangement is associated as said output layout.

10. The ophthalmic observation apparatus according to claim 6, wherein said plurality of operation modes includes a macular-degeneration examination mode for performing macular-degeneration examinations, and in said operation mode information, in relation to said macular-degeneration examination mode: a macula fixation direction for irradiating the macula and the surrounding area with said signal light is associated as said fixation direction; a three-dimensional scan that sequentially irradiates said signal light on a plurality of irradiation positions arranged in the form of lattice points is associated as said scanning pattern; a three-dimensional image of the macula and the surrounding area is associated as said image type; a retinal thickness analysis that obtains the retinal thickness and compares it with a prescribed standard thickness, and a drusen analysis that obtains the distribution of drusen are associated as said analytic processing; a tomographic image, the results of said retinal thickness analysis, and the results of said drusen analysis are associated as said information type; and a macular-degeneration diagnosis template that arranges said tomographic image, the results of said retinal thickness analysis, and the results of said drusen analysis in a prescribed arrangement is associated as said output layout.

11. The ophthalmic observation apparatus according to claim 6, further comprising:

an input means that inputs patient identification information, wherein said control means the operation mode for each examination in said storage means together with said input patient identification information, when patient identification information is input by said input means, said designating means retrieves the operation mode stored together with this patient identification information in the past from said storage means, and said control means controls said optical system, said image forming means, said analysis means, and/or said output means based on the operational details associated with said retrieved operation mode.

12. The ophthalmic observation apparatus according to claim 6, further comprising:

an input means that inputs patient identification information, and a timekeeping means that keeps the current date and time, wherein in said operation mode information, said operation mode is associated with an examination interval representing the time interval for performing examinations in the operation mode, said control means stores the operation mode for each examination in said storage means together with said input patient identification information and said kept date and time, when patient identification information is input by said input means, said designating means retrieves the operation mode and date and time stored together with this patient identification information in the past from said storage means, calculates the difference between said retrieved past date and time with the current date and time being kept by said timekeeping means to obtain the examination interval, and selects the operation mode associated with said obtained examination interval from among said plurality of operation modes, and said control means controls said optical system, said image forming means, said analysis means, and/or said output means based on the operational details associated with said selected operation mode.

13. The ophthalmic observation apparatus according to claim 6, further comprising:

an input means that inputs patient identification information, wherein if an abnormality is present in the analysis results obtained by said analysis means, said control means stores abnormal-presence information indicating as such in said storage means together with said input patient identification information, in said operation mode information, said operation mode is associated with operational-change information representing changes to the operational details if said abnormality is present, when patient identification information is input by said input means, said designating means retrieves abnormal-presence information stored together with this patient identification information in the past from said storage means, and if said abnormal-presence information is retrieved, changes the operational details of said operation mode based on said operational-change information, and said control means controls said optical system, said image forming means, said analysis means, and/or said output means based on the operational details after said change.

14. The ophthalmic observation apparatus according to claim 6, further comprising:

an image-capturing means that irradiates the fundus of the subject eye with illuminating light and receives light reflected from the fundus from this illuminating light to form a captured image of said fundus, wherein in said operation mode information, at least one of said plurality of operation modes is associated with the operational details of said image-capturing means, and if the operational details of said image-capturing means are associated with the operation mode designated by said designating means, said control means controls said image-capturing means based on the operational details to form a captured image of said fundus.

15. The ophthalmic observation apparatus according to claim 6, further comprising:

an operation means that is used for editing the operational details associated with said operation mode according to said operation mode information.

16. An ophthalmic observation apparatus comprising:

an optical system that divides light output from a light source unit into a signal light and a reference light, overlaps said signal light that has passed through a subject eye and the reference light that has passed through a reference light path, and generates and detects interference light;

an image forming means that, based on the detection results of said interference light by said optical system, forms an image of said subject eye;

an analysis means that analyzes said formed image;

an output means that outputs examination-results information including the image analysis results by said analysis means;

a storage means that preliminarily stores operation mode information in which each of a plurality of operation modes corresponding to examination types is associated with the operational details of at least one of said optical system, said image forming means, said analysis means, and said output means;

a designating means that designates one of said plurality of operation modes;

a control means that refers to the operation mode information stored in said storage to identify the operational details associated with said designated operation mode, and controls said optical system, said image forming means, said analysis means, and/or said output means based on said identified operational details;

an input means that inputs patient identification information; and a timekeeping means that keeps the current date and time, wherein in said operation mode information, said operation mode is associated with an examination interval representing the time interval for performing examinations in the operation mode, said control means stores the operation mode for each examination in said storage means together with said input patient identification information and said kept date and time, when patient identification information is input by said input means, said designating means retrieves the operation mode and date and time stored together with this patient identification information in the past from said storage means, calculates the difference between said retrieved past date and time with the current date and time being kept by said timekeeping means to obtain the examination interval, and selects the operation mode associated with said obtained examination interval from among said plurality of operation modes, and said control means controls said optical system, said image forming means, said analysis means, and/or said output means based on the operational details associated with said selected operation mode.

17. An ophthalmic observation apparatus comprising:

an optical system that divides light output from a light source unit into a signal light and a reference light, overlaps said signal light that has passed through a subject eye and the reference light that has passed through a reference light path, and generates and detects interference light;

an image forming means that, based on the detection results of said interference light by said optical system, forms an image of said subject eye;

an analysis means that analyzes said formed image;

an output means that outputs examination-results information including the image analysis results by said analysis means;

a storage means that preliminarily stores operation mode information in which each of a plurality of operation modes corresponding to examination types is associated with the operational details of at least one of said optical system, said image forming means, said analysis means, and said output means;

a designating means that designates one of said plurality of operation modes;

a control means that refers to the operation mode information stored in said storage to identify the operational details associated with said designated operation mode, and controls said optical system, said image forming means, said analysis means, and/or said output means based on said identified operational details; and an input means that inputs patient identification information, wherein if an abnormality is present in the analysis results obtained by said analysis means, said control means stores abnormal-presence information indicating as such in said storage means together with said input patient identification information, in said operation mode information, said operation mode is associated with operational-change information representing changes to the operational details if said abnormality is present, when patient identification information is input by said input means, said designating means retrieves abnormal-presence information stored together with this patient identification information in the past from said storage means, and if said abnormal-presence information is retrieved, changes the operational details of said operation mode based on said operational-change information, and said control means controls said optical system, said image forming means, said analysis means, and/or said output means based on the operational details after said change.

* * * * *